United States Patent [19]
Dowell et al.

[11] Patent Number: 5,859,000
[45] Date of Patent: Jan. 12, 1999

[54] METHOD FOR REDUCING MAST CELL MEDIATED ALLERGIC REACTIONS

[75] Inventors: Tad Dowell; Steven D. Norton; Barbara A. Araneo, all of Salt Lake City, Utah

[73] Assignees: University of Utah Research Foundation; Pharmadigm, Inc., both of Salt Lake City, Utah

[21] Appl. No.: 966,385

[22] Filed: Nov. 7, 1997

Related U.S. Application Data

[63] Continuation-in-part of Ser. No. 870,234, Jun. 5, 1997, Ser. No. 580,716, Dec. 29, 1995, Pat. No. 5,753,640, and Ser. No. 516,540, Aug. 15, 1995, said Ser. No. 580,716, is a continuation-in-part of Ser. No. 516,540, Aug. 15, 1995, which is a continuation-in-part of Ser. No. 480,747, Jun. 7, 1995.

[51] Int. Cl.⁶ .................................................. A61K 31/56
[52] U.S. Cl. ........................................... 514/178; 514/170
[58] Field of Search ...................................... 514/170, 178

[56] References Cited

U.S. PATENT DOCUMENTS

| 5,489,581 | 2/1996 | Daynes et al. | 514/170 |
| 5,532,230 | 7/1996 | Daynes et al. | 514/178 |
| 5,540,919 | 7/1996 | Daynes et al. | 424/85.2 |

*Primary Examiner*—Raymond J. Henley, III
*Attorney, Agent, or Firm*—Rothwell, Figg, Ernst & Kurz, P.C.

[57] ABSTRACT

The present invention is directed to a method for reducing mast cell mediated allergic reactions, including mast cell mediated allergy and asthma. Mast cell mediated allergic reactions, including type I hypersensitivity reasponse to allergens and asthma, are reduced by administering a dehydroepiandrosterone (DHEA) derivative to a patient in a manner which quickly raises blood levels of the active agent.

15 Claims, 5 Drawing Sheets

METHOD FOR REDUCING MAST CELL MEDIATED ALLERGIC REACTIONS

CROSS-REFERENCE TO RELATED APPLICATIONS

The present application is a continuation-in-part of application Ser. No. 08/870,234 filed 5 Jun. 1997, of application Ser. No. 08/580,716 filed 29 Dec. 1995 now U.S. Pat. No. 5,753,640 and of application Ser. No. 08/516,540, filed 15 Aug. 1995. Application Ser. No. 08/580,716 now U.S. Pat. No. 5,573,640 is in turn a continuation-in-part application of Ser. No. 08/516,540. Ser. No. 08/516,540 is in turn a continuation-in-part application of Ser. No. 08/480,747, filed 7 Jun. 1995. Each of these applications is incorporated herein by reference.

BACKGROUND OF THE INVENTION

The present invention is related to a method for reducing the effects of mast cell mediated allergic reactions, including mast cell mediated allergy and asthma. In accordance with the present invention, these allergic reactions are reduced by administering a dehydroepiandrosterone (DHEA) derivative.

The publications and other materials used herein to illuminate the background of the invention, and in particular cases, to provide additional details respecting the practice, are incorporated by reference, and for convenience are numerically referenced in the following text and respectively grouped in the appended bibliography.

Dehydroepiandrosterone (DHEA), a weak androgen, serves as the primary precursor in the biosynthesis of both androgens and estrogens (1). DHEA has been reported to play a mitigating role in obesity, diabetes, carcinogenesis, autoimmunity, neurological loss of memory (2–5), and the negative effects of GCS on IL-2 production by murine T cells (6).

Recent insight into the mechanism of action of DHEA has come from studies of ischemia-induced reperfusion injury. The clinical term used to describe the pathological process of wound extension is progressive dermal ischemia and it appears to represent the consequences of a host-initiated, time-dependent reperfusion injury. DHEA, DHEAS, DHEA congeners and DHEA derivatives have been found to either reduce or protect thermally injured mice against reperfusion damage of the microvasculature. Additionally, intervention therapy with the active agent could be withheld for up to 4 hours after burn with substantial therapeutic benefit. It has been observed that the immediate response to a burn injury is in many ways similar to an experiment reperfusion injury in other tissues. Studies suggest that DHEA, either directly or indirectly, through its action on endothelium prevents damage to the microvasculature in reperfusion injury.

In another study the effect of DHEA on ischemia/reperfusion injury of the isolated rat cremaster muscle was evaluated. The experimental approach employed intravital microscopy to establish whether DHEA pre-treatment of rats prior to ischemia/reperfusion of the isolated muscle would protect against damage to the capillaries and venules of microcirculation. These studies indicated that in control animals, 6 hours of ischemia followed by re-flow analysis at 90 minutes and 24 hours lead to insufficient perfusion of the muscle. In DHEA pre-treated rats, 6 hours of ischemia followed by re-flow analysis at 90 minutes, 24 hours and even 4 days showed normal perfusion values in the isolated muscle. In addition, it was clear that the DHEA pre-treatment prevented sticking of neutrophils to endothelium.

Additional studies in a global ischemic model demonstrated the protective effect of DHEA given intravenously after resuscitation of clinically dead rats.

Bacterial translocation is the process by which indigenous gut flora penetrate the intestinal barrier and invade sterile tissue. Included in this process is the migration of microbial organisms to the draining mesenteric lymph nodes, spleen, liver, blood and in some instances, the lung (7, 8). This phenomenon has been documented in humans following thermal injury (9–11) and ischemia-reperfusion injury (12). DHEA, DHEAS, DHEA congeners and DHEA derivatives have been found to either reduce or prevent bacterial translocation.

The evidence implicating the role of neutrophils in adult respiratory distress syndrome (ARDS) is substantial but indirect (13). Some of the first suggestions that neutrophils may cause an ARDS-like picture were found in severely neutropenic patients who were infused intravenously with donor neutrophils. Occasionally, within hours of neutrophil infusion, there was an abrupt "white-out" of the lungs (by x-ray) and onset of ARDS symptoms. Numerous studies have shown that neutrophils accumulate in the lung during ARDS. For example, their presence has been demonstrated histologically. During the early phases of ARDS, the number of circulating whole blood cells transiently decreases, probably due to their abnormal pulmonary sequestration. Some neutrophils that accumulate within lung capillaries leave the vascular space and migrate into the interstitium and alveolar airspaces. In normal healthy volunteers, neutrophils account for less than 3% of the cells that can be obtained by bronchoalveolar lavage (BAL). In patients with ARDS, the percentage of neutrophils in the lavage is markedly increased to 76–85%. The accumulation of neutrophils is associated with evidence of their activation. They demonstrate enhanced chemotaxis and generate abnormally high levels of oxygen metabolites following in vitro stimulation. Elevated concentrations of neutrophil secretory products, such as lactoferrin, have been detected in the plasma of patients with ARDS. Further evidence that neutrophils actively participate in lung injury was obtained from a clinical study of patients with mild lung injury who were neutropenic for an unrelated reason (e.g., receiving chemotherapy). It was noted that lung impairment frequently worsened if a patients hematological condition improved and circulating neutrophil counts recovered to normal levels.

As further proof that stimulated neutrophils can independently injure lung tissue, in vitro experiments have been performed using vascular endothelial and lung epithelial cells as targets. In some reports, neutrophils have been shown to detach endothelial cells or alveolar epithelial cells from the surface of the tissue culture dish. Obviously, if such an event were to occur in vivo, the denuded surfaces would permit substantial leakage of plasma contents. Furthermore, many reports have provided clear evidence that stimulated neutrophils are able to facilitate lysis of cultured vascular endothelial cells and alveolar epithelial cells. DHEA, DHEAS, DHEA congeners and DHEA derivatives have been found to either reduce or prevent ARDS.

In the United States, chronic obstructive pulmonary disease (COPD) represents the fifth most common cause of death (14). COPD also constitutes one of the most important causes of work incapacity and restricted activity (15). COPD, along with many other pulmonary diseases, causes pulmonary hypertension and right ventricular hypertrophy or cor pulmonale. Over 12 million patients in the United States alone have chronic bronchitis or emphysema, and approximately 3 million are chronically hypoxic with $PaO_2<60$ mmHg. These patients develop hypoxic pulmonary vasoconstriction, and eventually, right ventricular hypertrophy (16). Once right ventricular hypertrophy develops, the three-year mortality rate of those patients is 60% (17, 18). Irrespective of the current management, morbidity and mortality of patients with COPD and pulmonary hypertension remain high.

One model to study pulmonary hypertension is the pulmonary vasoconstriction induced by alveolar hypoxia. Experiments in isolated animal (19) and human (20) pulmonary arteries suggest that hypoxia-induced pulmonary vasoconstriction is mediated by a direct effect of hypoxia on pulmonary vascular smooth muscle cell. It has been reported (21) that hypoxia can depolarize the pulmonary vascular smooth muscle membrane by inducing an increase in tissue $Na^+$ and a decrease in $K^+$. More recently, it has been reported that hypoxia can alter the membrane potential in rat main pulmonary artery smooth muscle cell and can stimulate $Ca^{2+}$ influx through voltage-gated channels (22). There is strong evidence that $Ca^{2+}$ entry blockade can attenuate hypoxic pulmonary vasoconstriction in isolated rat lung (23) and in patients with chronic obstructive lung disease (24). Conceivably, hypoxia may effect other membrane transport mechanisms that are involved in $Ca^{2+}$ influx and/or efflux. For example, Voelkel et al. (25) speculated that hypoxia may impair $Ca^{2+}$ extrusion. Farrukh et al. (26) has demonstrated that cAMP and cGMP reverse hypoxic pulmonary vasoconstriction by stimulating $Ca^{2+}$ ATP-ase-dependent $Ca^{2+}$ extrusion and/or redistribution. DHEA, DHEAS, DHEA congeners and DHEA derivatives have been found to either reduce or prevent pulmonary hypertension.

The above findings, as well as the finding that DHEA, DHEAS, DHEA congeners and DHEA derivatives reduce the expression of p-selectin by endothelial cells, are shown in, for example, U.S. Pat. Nos. 5,489,581; 5,532,230; 5,583,126; 5,587,369; and 5,635,496 and the published application of PCT/US95/10990, all incorporated by reference herein.

Allergic diseases are mediated, at least in part, by IgE antibody; IgE antibody production is a central feature of allergic diseases. These include food allergy, stinging insect allergy, latex allergy, and anaphylaxis, allergic rhinitis, and asthma. It will also deal briefly with diseases such as atopic dermatitis, whose pathogenesis is obscure but is likely to be related to other allergic diseases. The chapter focuses on human systems but includes some results with rodent models.

Allergic diseases affect 20% to 30% of the population of the United States (27). It may suggest some selective advantages to being a patient with these diseases. The majority of patients with allergic diseases are atopic. Atopic individuals produce IgE antibody to airborne allergens such as proteins in ragweed and/or grass pollens and/or dust mites, and they express allergic rhinitis and/or asthma and/or atopic dermatitis. Food allergy is often the first manifestation of allergic diseases in young atopic children. Moreover, there is a strong genetic component to the atopic state.

The expression of allergic disease requires a number of sequential events, including exposure to allergens, induction of IgE antibody production, binding of IgE to he surface receptors of mast cells and basophils, re-exposure to allergen, binding of allergen to cell-associated IgE, signal transduction in mast cells and basophils, mediator secretion, and mediator effects on end-organs such as blood vessels and bronchial smooth muscle.

As defined by Coombs and Gell (28), hypersensitivity reactions can be subdivided into four types, called 1,11, 111, and IV, which represent four distinct immune mechanisms that result in tissue injury. A subdivision of type IV reactions into IV A and IV B is also described below. This classification is outlined schematically in Table 1. These same four processes represent mechanisms of immune protection from infectious agents, as described below.

Type I reactions are "immediate hypersensitivity," or classical allergic reactions. These reactions occur within 15 mins following interaction of soluble antigen with mast cell-bound IgE antibody. The pathology is related to mast cell degranulation, and the reaction is driven by mast cell mediators such as histamine and leukotriene C4 (LTC4). An example of an in vivo counterpart is an urticarial reaction following injection of penicillin in a penicillin-allergic patient. The importance of type I reactions in protection from infectious organisms is uncertain, although the increased vascular permeability mediated by these reactions probably facilitates the capacity of antibody and inflammatory cells to arrive at the infected site (29).

Substances that induce symptoms of immediate hypersensitivity by inducing IgE antibody responses are termed allergens. Most atopic individuals produce IgE antibody to a long list of aeroallergens, that is, allergens found in the air. These allergens induce sensitization via exposure to the afferent immune system in the nasal or respiratory tract. A variety of allergens, derived from outdoor and indoor airborne sources, foods, and insect venoms, have been cloned and sequenced. The T-cell response pattern to allergens appears to be quite similar to that of conventional antigens, in that antigenic fragments are presented via MHC class II molecules on antigen-presenting cells to the T-cell receptor (30). Immunodominant peptides have been identified on several allergens; these have generally been DR-restricted, but recent studies have identified DP-restricted responses (31). The dose of exposure, the route of exposure (e.g., what type of particulate), and the genetic background of the host all interact to determine the magnitude of the IgE response to allergens. The levels of exposure to airborne allergens are quite low, suggesting that immune response genes may be identified that determine responsiveness to specific allergen epitopes (32). Moreover, the reasons why atopic patients produce IgE and make other immune responses to airborne allergens, while nonatopic patients do not, are not explained.

IgE antibodies are preferentially formed in response to parasitic antigens or allergens. Although low in concentration, IgE antibodies bind with high affinity to specific receptors (FcεRI) on mast cells and basophils. Antigen cross-linking of IgE molecules and the receptors to which they attach initiates the release or production of a variety of cellular mediators. The mediators begin a series of physiologic events that lead to allergic diseases, such as allergic rhinitis, asthma and urticaria, but they may also help to confer specific protective immunity against parasites.

Antigen-mediated crosslinking of FcεRI results in secretion of mediators from mast cells. Both the morphology of the mast cells and the mediator levels in tissue fluids confirm that mast cell degranulation occurs in vivo during allergic reactions (33, 34). The mediators secreted by mast cells and basophils account for the symptoms of allergic reactions (35). These include the following preformed mediators, which are associated with granules: histamine (bound to sulfated proteoglycans, either heparin or chondroitin sulfate), the proteoglycans themselves, and several proteases, including the neutral proteases, carboxypeptidase (s), tryptase, and (in some mast cells) chymase. The cytokine TNF-α is released in part from a stored form in mast cells (36), but this cytokine is not stored in macrophages or T cells. In addition, there are newly synthesized molecules, including LTC4, PGD2, and PAF, and cytokines.

Asthma is a chronic disease of the large and small airways of the lung (37–39) which affects 5% to 10% of the population. The disease is more common in children, but may persist for years and may develop only in adult life. Asthma is characterized by several clinical and pathological features. The most prominent feature is bronchospasm, or narrowing of the airways; the bronchospasm is often reversible over time or with treatment. Asthmatic patients have prominent contraction of the smooth muscle of large and small airways, an increased mucus production, and an inflammatory infiltrate consisting of eosinophils, as well as basophils and T lymphocytes; epithelial cell shedding occurs (40, 41). Airway narrowing is due not only to bronchial smooth muscle contraction, but also to mucus production and inflammation. Important laboratory findings include evidence of airway narrowing, increased numbers of circulating eosinophils, and moderate increases in total serum IgE (compared to nonasthmatic patients of the same age). A substantial number of patients are atopic and a substantial number express IgE antibody against specific allergens such as dust mite (42). One additional finding is airway hyperreactivity. That is, while stimuli that induce smooth muscle contraction, such as histamine and methacholine (an acetylcholine-like agent), may induce bronchospasm in all individuals, much lower concentrations of these bronchospastic agents are required in order to induce bronchoconstriction in hyperreactive individuals.

The mechanisms that induce all the pathologic findings in asthma are not known. In many patients with asthma, allergen exposure may induce a fall-blown, severe episode of airway inflammation. In such patients, the mechanisms are presumed to be the same as those that induce a pulmonary LPR after inhalation of allergen: that is, allergen crosslinks mast cell-associated IgE antibody, which in turn leads to the release of mast cell mediators.

Mast cell mediators such as histamine and LTC4 are important inducers of bronchospasm and mucus production. Cytokines, perhaps derived from mast cells or T cells (which may interact with antigen processed by an antigen-presenting cell), induce inflammation. Eosinophil-derived mediators, such as major basic protein, peroxidase, and cationic protein, appear to be important in inducing epithelial injury (40, 43). There also appear to be antigen-independent mechanisms of inducing asthma, including viral infection and exercise. It is possible that these other mechanisms are also initiated by a common pathway of mast cell activation (although many investigators believe that mast cells are not of central importance). It is likely that eosinophils are an important mediator of asthma; in patients, levels of circulating eosinophils increase when asthma worsens. Moreover, glucocorticoids are effective in treating moderate and severe asthma and in reducing levels of circulating and tissue eosinophils.

Several abnormalities may be present in patients with asthma. They not only tend to be atopic, and thus have increased tendency to produce IgE antibodies to allergens, but their basophils tend to secrete mediators more readily in response to certain stimuli (44). Furthermore, many patients with asthma have been reported to have several abnormalities of autocrine or neuropeptide receptors. Some years ago, it was noted that asthmatic patients had a generalized decrease in β-adrenergic receptor (which mediates smooth muscle relaxation) responsiveness and increased cholinergic and β-adrenergic (which mediates smooth muscle contraction) responsiveness; indeed, some of these patients have circulating antibodies to β-adrenergic receptors. However, these findings are not specific for asthma (45). More recently, asthmatic patients have been reported to have a decrease in receptors for vasoactive intestinal peptide (a ligand that relaxes smooth muscle) and perhaps an increase in receptors for substance P (a ligand that contracts smooth muscle) (46, 47).

Several non-IgE pathways result in asthma. Viral infections are associated with concomitant worsening of pulmonary function (38). Nonsteroidal anti-inflammatory agents, such as aspirin, may exacerbate asthma; about 5% of asthmatic patients are sensitive to these agents (48). It has been hypothesized that these agents act by altering the metabolism of arachidonic acid, since these agents block prostaglandin synthetase. However, the precise mechanism is unknown. Another cause of asthma is exercise, apparently because of a fall in temperature and humidity of the airway. The mechanisms are not clear. One interesting hypothesis, that exercise-induced asthma results from inducing local hyperosmolarity, which is in turn a trigger for mast cell activation, has not been confirmed. Among all these non-IgE pathways, whether mast cell mediator release has a role is arguable.

One of the most interesting areas of recent investigation concerns the role of allergens. Case-control studies of emergency room admissions with asthma have established that IgE antibodies to certain allergens, namely, "indoor allergens" from dust mite, cat, and cockroach, are important risk factors (37, 49). Other studies have shown that, in allergic patients, inhalational challenge with these allergens induces an inflammatory LPR and bronchial hyperreactivity. Dust mite-sensitive patients with asthma, when moved into an environment free of dust mites, may exhibit a dramatic improvement in symptoms (50). These latter findings are provocative, although they need to be repeated in a controlled study. Unexpectedly, improvement of some patients required months; there is no obvious explanation for this. As previously noted, other studies with dust mites suggest that high dust mite exposure in the first two years of life is predictive of the presence of asthma at age 10. Consequently, environmental control of these allergens is being tested for its effectiveness in treating asthma. In addition, immunotherapy (see below) is effective in treating some patients with allergen-induced asthma.

Environmental factors other than allergens may be important in asthma. Certain chemicals, such as ozone and nitric oxide, are reported to worsen asthma (51, 52). Also, passive cigarette smoke exposure worsens asthma (53).

Within the last 10 years, the incidence of asthma, its severity, and deaths from asthma have increased. The increase in asthma morbidity and mortality is most striking in children, and in the United States the morbidity and mortality are highest in African-American children in the inner city (54). These epidemiologic trends have not yet been adequately explained. One interesting idea is that, in attempts to improve the energy efficiency of homes, these homes have become "tighter" and less leaky and have allowed the concentrations of allergens and other adverse environmental factors to increase (55).

It is desired to identify compounds which are useful in the treatment of mast cell mediated allergic reactions, including type I hypersensitivity response to allergens and asthma.

SUMMARY OF THE INVENTION

The present invention is directed to a method for reducing mast cell mediated allergic reactions, including mast cell mediated allergy and asthma. Mast cell mediated allergic reactions, including type I hypersensitivity reasponse to allergens and asthma, are reduced by administering a dehydroepiandrosterone (DHEA) derivative to a patient in a manner which quickly raises blood levels of the active agent.

DETAILED DESCRIPTION OF THE INVENTION

Figure 1A:
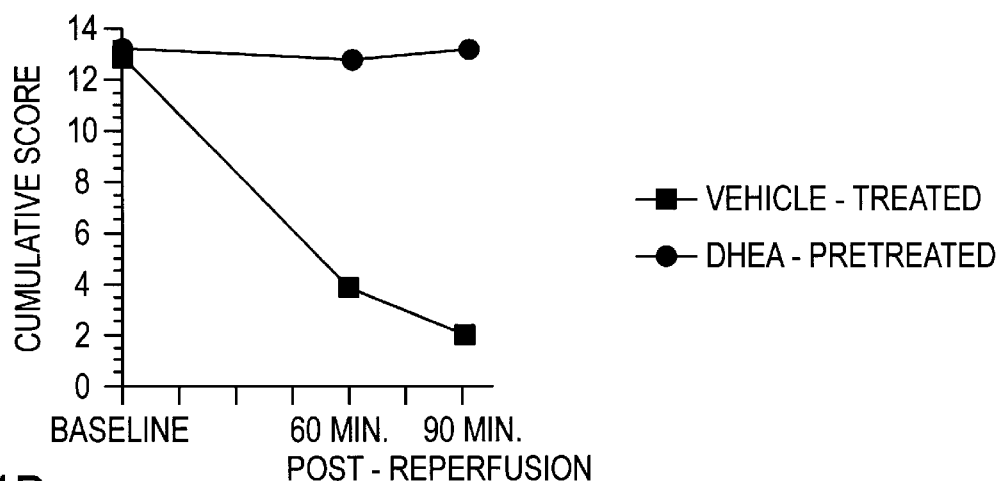
FIG. 1A shows the number of flowing capillaries in proximity to post-capillary venule in Zone 1 during reperfusion injury.

The present invention is directed to a method for reducing mast cell mediated allergic reactions, including mast cell mediated allergy and asthma. Mast cell mediated allergic reactions, including type I hypersensitivity reasponse to allergens and asthma, are reduced by administering a dehydroepiandrosterone (DHEA) derivative to a patient in a manner which quickly raises blood levels of the active agent. Any method which quickly raises the blood levels of the active agent can be utilized, although it is preferred to administer the active agent intraveneously, intraperitonealy or intramuscularly.

Examples of a DHEA derivative, include but are not limited to, compounds having the general formulas I and II and their pharmaceutically acceptable salts

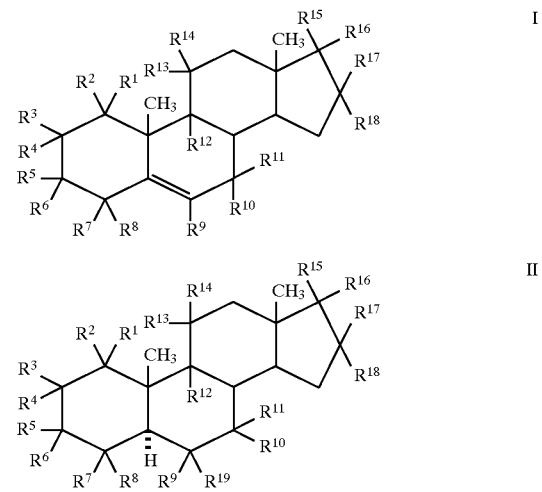

wherein
$R^1, R^2, R^3, R^4, R^6, R^7, R^8, R^9, R^{10}, R^{12}, R^{13}, R^{14}$ and $R^{19}$ are independently H, OH, halogen, $C_{1-10}$ alkyl or $C_{1-10}$ alkoxy;

$R^5$ and $R^{11}$ are independently OH, SH, H, halogen, pharmaceutically acceptable ester, pharmaceutically acceptable thioester, pharmaceutically acceptable ether, pharmaceutically accceptable thioether, pharmaceutically acceptable inorganic esters, pharmaceutically acceptable monosaccharide, disaccharide or oligosaccharide, spirooxirane, spirothirane, $-OSO_2R^{20}$, $-OPOR^{20}R^{21}$ or $C_{1-10}$ alkyl; or $R^5$ and $R^6$ taken together are =O; or
$R^{10}$ and $R^{11}$ taken together are =O;
$R^{15}$ is (1) H, halogen, $C_{1-10}$ alkyl or $C_{1-10}$ alkoxy when $R^{16}$ is $-C(O)OR_{22}$ or (2) H, halogen, OH or $C_{1-10}$ alkyl when $R^{16}$ is halogen, OH or $C_{1-10}$ alkyl or (3) H, halogen, $C_{1-10}$ alkyl, $C_{1-10}$ alkenyl, $C_{1-10}$ alkynyl, formyl, $C_{1-10}$ alkanoyl or epoxy when $R^{16}$ is OH; or (4) OH, SH, H, halogen, pharmaceutically acceptable ester, pharmaceutically acceptable thioester, pharmaceutically acceptable ether, pharmaceutically accceptable thioether, pharmaceutically acceptable inorganic esters, pharmaceutically acceptable monosaccharide, disaccharide or oligosaccharide, spirooxirane, spirothirane, $-OSO_2R^{20}$ or $-OPOR^{20}R^{21}$ when $R^{16}$ is H; or $R^{15}$ and $R^{16}$ taken together are =O;
$R^{17}$ and $R^{18}$ are independently (1) H, $-OH$, halogen, $C_{1-10}$ alkyl or $C_{1-10}$ alkoxy when $R^{16}$ is H, OH, halogen, $C_{1-10}$ alkyl or $-C(O)OR^{22}$ or (2) H, $(C_{1-10}$ alkyl$)_n$amino, $(C_{1-10}$alkyl$)_n$amino-$C_{1-10}$ alkyl, $C_{1-10}$ alkoxy, hydroxy-$C_{1-10}$alkyl, $C_{1-10}$ alkoxy-$C_{1-10}$ alkyl, (halogen)$_m$-$C_{1-10}$ alkyl, $C_{1-10}$ alkanoyl, formyl, $C_{1-10}$ carbalkoxy or $C_{1-10}$ alkanoyloxy when $R^{15}$ and $R^{16}$ taken together are =O; or $R^{17}$ and $R^{18}$ taken together are =O or taken together with the carbon to which they are attached form a 3–6 member ring containing 0 or 1 oxygen atom; or $R^{15}$ and $R^{17}$ taken together with the carbons to which they are attached form an epoxide ring;

$R^{20}$ and $R^{21}$ are independently OH, pharmaceutically acceptable ester or pharmaceutically acceptable ether;

$R^{22}$ is H, (halogen)$_m$-$C_{1-10}$ alkyl or $C_{1-10}$ alkyl;

n is 0, 1 or 2; and m is 1, 2or 3.

Compounds of general formulas I and II are synthesized as described in U.S. Pat. Nos. 4,898,694; 5,001,119; 5,028,631; and 5,175,154, incorporated herein by reference. The compounds represented by the general formulas I and II exist is many stereoisomers and these formulas are intended to encompass the various stereoisomers.

Examples of suitable DHEA derivatives include compounds in which:

(1) $R^{15}$ and $R^{16}$ taken together are =O, $R^6$ is H and $R^5$ is OH, pharmaceutically acceptable esters thereof, pharmaceutically acceptable ethers thereof or pharmaceutically acceptable salts, or $R^5$ and $R^6$ taken together are =O, and $R^1$, $R^2$, $R^3$, $R^4$, $R^7$, $R^8$, $R^9$, $R^{10}$, $R^{11}$, $R^{12}$, $R^{13}$, $R^{14}$, $R^{17}$, $R^{18}$ and $R^{19}$ are each H;

(2) $R^{15}$ and $R^{16}$ taken together are =O, $R^6$ is H and $R^5$ is OH, pharmaceutically acceptable esters thereof, pharmaceutically acceptable ethers thereof or pharmaceutically acceptable salts, or $R^5$ and $R^6$ taken together are =O, $R^{17}$ is halogen and $R^1$, $R^2$, $R^3$, $R^4$, $R^7$, $R^8$, $R^9$, $R^{10}$, $R^{11}$, $R^{12}$, $R^{13}$, $R^{14}$, $R^{18}$ and $R^{19}$ are each H;

(3) $R^{15}$ and $R^{16}$ taken together are =O, $R^5$ is SH, pharmaceutically acceptable thioesters thereof, pharmaceutically acceptable thioethers thereof or pharmaceutically acceptable salts, and $R^1$, $R^2$, $R^3$, $R^4$, $R^6$, $R^7$, $R^8$, $R^9$, $R^{10}$, $R^{11}$, $R^{12}$, $R^{13}$, $R^{14}$, $R^{17}$, $R^{18}$ and $R^{19}$ are each H;

(4) $R^{15}$ and $R^{16}$ taken together are =O, $R^5$ is SH, pharmaceutically acceptable thioesters thereof, pharmaceutically acceptable thioethers thereof or pharmaceutically acceptable salts, $R^{17}$ is halogen, and $R^1$, $R^2$, $R^3$, $R^4$, $R^6$, $R^7$, $R^8$, $R^9$, $R^{10}$, $R^{11}$, $R^{12}$, $R^{13}$, $R^{14}$, $R^{18}$ and $R^{19}$ are each H;

(5) $R^{15}$ and $R^{16}$ taken together are =O, $R^6$ and $R^{10}$ are H and $R^5$ and $R^{11}$ are independently OH, pharmaceutically acceptable esters thereof, pharmaceutically acceptable ethers thereof or pharmaceutically acceptable salts, or $R^5$ and $R^6$ taken together and $R^{10}$ and $R^{11}$ taken together are independently =O and $R^1$, $R^2$, $R^3$, $R^4$, $R^7$, $R^8$, $R^9$, $R^{12}$, $R^{13}$, $R^{14}$, $R^{17}$, $R^{18}$ and $R^{19}$ are each H;

(6) $R^{15}$ and $R^{16}$ taken together are =O, $R^6$ and $R^{10}$ are H and $R^5$ and $R^{11}$ are independently OH, pharmaceutically acceptable esters thereof, pharmaceutically acceptable ethers thereof or pharmaceutically acceptable salts, or $R^5$ and $R^6$ taken together and $R^{10}$ and $R^{11}$ taken together are independently =O, R is halogen, and $R^1$, $R^2$, $R^3$, $R^4$, $R^7$, $R^8$, $R^9$, $R^{12}$, $R^{13}$, $R^{14}$, $R^{18}$ and $R^{19}$ are each H;

(7) $R^{15}$ and $R^{16}$ taken together are =O, $R^5$ and $R^{11}$ are independently SH, pharmaceutically acceptable thioesters thereof, pharmaceutically acceptable thioethers thereof or pharmaceutically acceptable salts, and $R^1$, $R^2$, $R^3$, $R^4$, $R^6$, $R^7$, $R^8$, $R^9$, $R^{10}$, $R^{12}$, $R^{13}$, $R^{14}$, $R^{17}$, $R^{18}$ and $R^{19}$ are each H;

(8) $R^{15}$ and $R^{16}$ taken together are =O, $R^5$ and $R^{11}$ are independently SH, pharmaceutically acceptable thioesters thereof, pharmaceutically acceptable thioethers thereof or pharmaceutically acceptable salts, R is halogen, and $R^1$, $R^2$, $R^3$, $R^4$, $R^6$, $R^7$, $R^8$, $R^9$, $R^{10}$, $R^{12}$, $R^{13}$, $R^{14}$, $R^{18}$ and $R^{19}$ are each H;

(9) $R^{15}$ is OH, $R^6$ is H and $R^5$ is OH, pharmaceutically acceptable esters thereof, pharmaceutically acceptable ethers thereof or pharmaceutically acceptable salts, or $R^5$ and $R^6$ taken together are =O, and $R^1$, $R^2$, $R^3$, $R^4$, $R^7$, $R^8$, $R^9$, $R^{10}$, $R^{12}$, $R^{13}$, $R^{14}$, $R^{16}$, $R^{17}$, $R^{18}$ and $R^{19}$ are each H;

(10) $R^{15}$ is OH, $R^3$ is H, $R^6$ is H and $R^5$ is OH, pharmaceutically acceptable esters thereof, pharmaceutically acceptable ethers thereof or pharmaceutically acceptable salts, or $R^5$ and $R^6$ taken together are =O, $R^{17}$ is halogen, and $R^1$, $R^2$, $R^3$, $R^4$, $R^7$, $R^8$, $R^9$, $R^{10}$, $R^{12}$, $R^{13}$, $R^{14}$, $R^{16}$, $R^{18}$ and $R^{19}$ are each H;

(11) $R^{15}$ is OH, $R^5$ is SH, pharmaceutically acceptable thioesters thereof, pharmaceutically acceptable thioethers thereof or pharmaceutically acceptable salts, and $R^1$, $R^2$, $R^3$, $R^4$, $R^6$, $R^7$, $R^8$, $R^9$, $R^{10}$, $R^{11}$, $R^{12}$, $R^{13}$, $R^{14}$, $R^{16}$, $R^{17}$, $R^{18}$ and $R^{19}$ are each H;

(12) $R^{15}$ is OH, $R^5$ is SH, pharmaceutically acceptable thioesters thereof, pharmaceutically acceptable thioethers thereof or pharmaceutically acceptable salts, $R^{17}$ is halogen, and $R^1$, $R^2$, $R^3$, $R^4$, $R^6$, $R^7$, $R^8$, $R^9$, $R^{10}$, $R^{11}$, $R^{12}$, $R^{13}$, $R^{14}$, $R^{16}$, $R^{18}$ and $R^{19}$ are each H;

(13) $R^{15}$ is OH, $R^6$ and $R^{10}$ are H and $R^5$ and $R^{11}$ are independently OH, pharmaceutically acceptable esters thereof, pharmaceutically acceptable ethers thereof or pharmaceutically acceptable salts, or $R^5$ and $R^6$ taken together and R and R taken together are independently =O, and $R^1$, $R^2$, $R^3$, $R^4$, $R^7$, $R^8$, $R^9$, $R^{12}$, $R^{13}$, $R^{14}$, $R^{16}$, $R^{18}$ and $R^{19}$ are each H;

(14) $R^{15}$ is OH, $R^6$ and $R^{10}$ are H and $R^5$ and $R^{11}$ are independently OH, pharmaceutically acceptable esters thereof, pharmaceutically acceptable ethers thereof or pharmaceutically acceptable salts, or $R^5$ and $R^6$ taken together and $R^{10}$ and $R^{11}$ taken together are independently =O, $R^{17}$ is halogen, and $R^1$, $R^2$, $R^3$, $R^4$, $R^7$, $R^8$, $R^9$, $R^{12}$, $R^{13}$, $R^{14}$, $R^{16}$, $R^{18}$ and $R^{19}$ are each H;

(15) $R^{15}$ is OH, $R^5$ and $R^{11}$ are independently SH, pharmaceutically acceptable thioesters thereof, pharmaceutically acceptable thioethers thereof or pharmaceutically acceptable salts, and $R^1$, $R^2$, $R^3$, $R^4$, $R^6$, $R^7$, $R^8$, $R^9$, $R^{10}$, $R^{12}$, $R^{13}$, $R^{14}$, $R^{16}$, $R^{17}$, $R^{18}$ and $R^{19}$ are each H;

(16) $R^{15}$ is OH, $R^5$ and $R^{11}$ are independently SH, pharmaceutically acceptable thioesters thereof, pharmaceutically acceptable thioethers thereof or pharmaceutically acceptable salts, $R^{17}$ is halogen, and $R^1$, $R^2$, $R^3$, $R^4$, $R^6$, $R^7$, $R^8$, $R^9$, $R^{10}$, $R^{12}$, $R^{13}$, $R^{14}$, $R^{16}$, $R^{18}$ and $R^{19}$ are each H;

(17) $R^{15}$ is SH, $R^6$ is H and $R^5$ is OH, pharmaceutically acceptable esters thereof, pharmaceutically acceptable ethers thereof or pharmaceutically acceptable salts, or $R^5$ and $R^6$ taken together are =O, and $R^1$, $R^2$, $R^3$, $R^4$, $R^7$, $R^8$, $R^9$, $R^{10}$, $R^{11}$, $R^{12}$, $R^{13}$, $R^{14}$, $R^{16}$, $R^{18}$ and $R^{19}$ are each H;

(18) $R^{15}$ is SH, $R^6$ is H and $R^5$ is OH, pharmaceutically acceptable esters thereof, pharmaceutically acceptable ethers thereof or pharmaceutically acceptable salts, or $R^5$ and $R^6$ taken together are =O, $R^{17}$ is halogen, and $R^1$, $R^2$, $R^3$, $R^4$, $R^7$, $R^8$, $R^9$, $R^{10}$, $R^{11}$, $R^{12}$, $R^{13}$, $R^{14}$, $R^{16}$, $R^{18}$ and $R^{19}$ are each H;

(19) $R^{15}$ is SH, $R^5$ is SH, pharmaceutically acceptable thioesters thereof, pharmaceutically acceptable thioethers thereof or pharmaceutically acceptable salts, and $R^1$, $R^2$, $R^3$, $R^4$, $R^6$, $R^7$, $R^8$, $R^9$, $R^{10}$, $R^{11}$, $R^{12}$, $R^{13}$, $R^{14}$, $R^{16}$, $R^{17}$, $R^{18}$ and $R^{19}$ are each H;

(20) $R^{15}$ is SH, $R^5$ is SH, pharmaceutically acceptable thioesters thereof, pharmaceutically acceptable thioethers thereof or pharmaceutically acceptable salts, $R^{17}$ is halogen, and $R^1$, $R^2$, $R^3$, $R^4$, $R^7$, $R^8$, $R^9$, $R^{10}$, $R^{11}$, $R^{12}$, $R^{13}$, $R^{14}$, $R^{16}$, $R^{18}$ and $R^{19}$ are each H;

(21) $R^{15}$ is SH, $R^6$ and $R^{10}$ are H and $R^5$ and $R^{11}$ are independently OH, pharmaceutically acceptable esters thereof, pharmaceutically acceptable ethers thereof or pharmaceutically acceptable salts, or $R^5$ and $R^6$ taken together and $R^{10}$ and RI taken together are independently =O, and $R^1$, $R^2$, $R^3$, $R^4$, $R^7$, $R^8$, $R^9$, $R^{12}$, $R^{13}$, $R^{14}$, $R^{16}$, $R^{18}$ and $R^{19}$ are each H;

(22) $R^{15}$ is SH, $R^6$ and $R^{10}$ are H and $R^5$ and $R^{11}$ are independently OH, pharmaceutically acceptable esters thereof, pharmaceutically acceptable ethers thereof or pharmaceutically acceptable salts, or $R^5$ and $R^6$ taken together and $R^{10}$ and $R^{11}$ taken together are independently =O, $R^{17}$ is halogen, and $R^1$, $R^2$, $R^3$, $R^4$, $R^7$, $R^8$, $R^9$, $R^{12}$, $R^{13}$, $R^{14}$, $R^{16}$, $R^{18}$ and $R^{19}$ are each H;

(23) $R^{15}$ is SH, $R^5$ and $R^{11}$ are independently SH, pharmaceutically acceptable thioesters thereof, pharmaceutically acceptable thioethers thereof or pharmaceutically acceptable salts, and $R^1$, $R^2$, $R^3$, $R^4$, $R^6$, $R^7$, $R^8$, $R^9$, $R^{10}$, $R^{12}$, $R^{13}$, $R^{14}$, $R^{16}$, $R^{17}$, $R^{18}$ and $R^{19}$ are each H;

(24) $R^{15}$ is SH, $R^5$ and $R^{11}$ are independently SH, pharmaceutically acceptable thioesters thereof, pharmaceutically acceptable thioethers thereof or pharmaceutically acceptable salts, $R^{17}$ is halogen, and $R^1$, $R^2$, $R^3$, $R^4$, $R^6$, $R^7$, $R^8$, $R^9$, $R^{10}$, $R^{12}$, $R^{13}$, $R^{14}$, $R^{16}$, $R^{18}$ and $R^{19}$ are each H;

(25) $R^6$, $R^{10}$ and $R^{16}$ are H and $R^5$, $R^{11}$ and $R^{15}$ are independently OH, a sugar residue, pharmaceutically acceptable esters thereof, pharmaceutically acceptable ethers thereof or pharmaceutically acceptable salts, or $R^5$ and $R^6$ taken together and $R^{10}$ and $R^{11}$ taken together and $R^{15}$ and $R^{16}$ taken together are independently =O, and $R^1$, $R^2$, $R^3$, $R^4$, $R^7$, $R^8$, $R^9$, $R^{12}$, $R^{13}$, $R^{14}$, $R^{17}$, $R^{18}$ and $R^{19}$ are each H, wherein at least one of $R^5$, $R^{11}$ and $R^{15}$ is a sugar residue;

(26) $R^6$, $R^{10}$ and $R^{16}$ are H and $R^5$, $R^{11}$ and $R^{15}$ are independently OH, a sugar residue, pharmaceutically acceptable esters thereof, pharmaceutically acceptable ethers thereof or pharmaceutically acceptable salts, or $R^5$ and $R^6$ taken together and $R^{10}$ and $R^{11}$ taken together and $R^{15}$ and $R^{16}$ taken together are independently =O, R is halogen, and $R^1$, $R^2$, $R^3$, $R^4$, $R^7$, $R^8$, $R^9$, $R^{12}$, $R^{13}$, $R^{14}$, $R^{18}$ and $R^{19}$ are each H, wherein at least one of $R^5$, $R^{11}$ and $R^{15}$ is a sugar residue;

(27) $R^6$, $R^{10}$ and $R^{16}$ are H and $R^5$, $R^{11}$ and $R^{15}$ are independently OH, pharmaceutically acceptable inorganic esters thereof or pharmaceutically acceptable salts, or $R^5$ and $R^6$ taken together and $R^{10}$ and $R^{11}$ taken together and $R^{15}$ and $R^{16}$ taken together are independently =O, and $R^1$, $R^2$, $R^3$, $R^4$, $R^7$, $R^8$, $R^9$, $R^{12}$, $R^{13}$, $R^{14}$, $R^{16}$, $R^{18}$ and $R^{19}$ are each H, wherein at least one of $R^5$, $R^{11}$ and $R^{15}$ is an inorganic ester;

(28) $R^6$, $R^{10}$ and $R^{16}$ are H and $R^5$, $R^{11}$ and $R^{15}$ are independently OH, pharmaceutically acceptable inorganic esters thereof or pharmaceutically acceptable salts, or $R^5$ and $R^6$ taken together and $R^{10}$ and $R^{11}$ taken together and $R^{15}$ and $R^{16}$ taken together are independently =O, $R^{17}$ is halogen, and $R^1$, $R^2$, $R^3$, $R^4$, $R^7$, $R^8$, $R^9$, $R^{12}$, $R^{13}$, $R^{14}$, $R^{18}$ and $R^{19}$ are each H, wherein at least one of $R^5$, $R^{11}$ and $R^{15}$ is an inorganic ester.

Pharmaceutically acceptable esters or thioesters include, but are not limited to, esters or thioesters of the formula —OOCR or —SOCR, wherein R is a pharmaceutically acceptable alkyl, alkenyl, aryl, alkylaryl, arylalkyl, spingosine or substituted spingolipid groups, such as propionate, enanthate, cypionate, succinate, decanoate and phenylpropionate esters.

Pharmaceutically acceptable ethers or thioethers include, but are not limited to, ethers or thioethers of the formula —OR or —SR, wherein R is as defined above or enol, or —OR is an unsubstituted or substituted spirooxirane or —SR is a spirothiane.

Suitable sugar residues include, but are not limited to monosaccharides, disaccharides and oligosaccharides, such as a glucuronate.

Pharmaceutically acceptable inorganic esters include, but are not limited to, inorganic esters of the formula —$OSO_2R^{20}$ or —$OPOR^{20}R^{21}$, wherein $R^{20}$ and $R^{21}$ are independently —OH, pharmaceutically acceptable esters, pharmaceutically acceptable ethers or pharmaceutically acceptable salts.

Examples of representative compounds which fall within the scope of general formulas I and II included the following:

5α-androstan-17-one;
16α-fluoro-5α-androstan-17-one;
3β-methyl-5α-androsten-17-one;
16α-fluoro-5α-androstan-17-one;
17β-bromo-5-androsten-16-one;
17β-fluoro-3β-methyl-5-androsten-16-one;
17α-fluoro-5α-androstan-16-one;
3β-hydroxy-5-androsten-17-one;
17α-methyl-5α-androstan-16-one;
16α-methyl-5-androsten-17-one;
3β,16α-dimethyl-5-androsten-17-one;
3β,17α-dimethyl-5-androsten-16-one;
16α-hydroxy-5-androsten-17-one;
16α-fluoro-16β-methyl-5-androsten-17-one;
16α-methyl-5α-androstan-17-one;
16-dimethylaminomethyl-5α-androstan-17-one;
16β-methoxy-5-androsten-17-one;
16α-fluoromethyl-5-androsten-17-one;
16-methylene-5-androsten-17-one;
16-cyclopropyl-5α-androstan-17-one;
16-cyclobutyl-5-androsten-17-one;
16-hydroxymethylene-5-androsten-17-one;
3α-bromo-16α-methoxy-5-androsten-17-one;
16-oxymethylene-5-androsten-17-one;
3β-methyl-16ξ-trifluoromethyl-5α-androstan-17-one;
16-carbomethoxy-5-androsten-17-one;
3β-methyl-16β-methoxy-5α-androstan-17-one;
3β-hydroxy-16α-dimethylamino-5-androsten-17-one;
17α-methyl-5-androsten-17β-ol;
17α-ethynyl-5α-androstan-17β-ol;
17β-formyl-5α-androstan-17β-ol;
20,21-epoxy-5α-pregnan-17α-ol;
3β-hydroxy-20,21-epoxy-5α-pregnan-17α-ol;
16α-fluoro-17α-ethenyl-5-androsten-17β-ol;
16α-hydroxy-5-androsten-17α-ol;
16α-methyl-5α-androstan-17α-ol;
16α-methyl-16β-fluoro-5α-androstan-17α-ol;
16α-methyl-16β-fluoro-3-hydroxy-5-androsten-17α-ol;
3β,16β-dimethyl-5-androsten-17β-ol;
3β,16,16-trimethyl-5-androsten-17β-ol;
3β,16,16-trimethyl-5-androsten-17-one;
3β-hydroxy-4α-methyl-5-androsten-17α-ol;

3α-hydroxy-4α-methyl-5-androsten-17-one;
3α-hydroxy-1α-methyl-5-androsten-17-one;
3α-ethoxy-5α-androstan-17β-ol;
5α-pregnan-20-one;
3β-methyl-5α-pregnan-20-one;
16α-methyl-5-pregnen-20-one;
16α-methyl-3β-hydroxy-5-pregnen-20-one;
17α-fluoro-5-pregnen-20-one;
21-fluoro-5α-pregnan-20-one;
17α-methyl-5-pregnen-20-one;
20-acetoxy-cis-17(20)-5α-pregnene;
3α-methyl-16,17-epoxy-5-pregnen-20-one.

It has been discovered that the administration to a patient of a therapeutically effective amount of DHEA, DHEAS, a DHEA congener or a DHEA derivative as defined by general formulas I and II above in a physiologically acceptable carrier is able to reduce or prevent mast cell mediated allergic reactions, including type I hypersensitivity response to allergens and asthma. The DHEA derivative is administered as soon as possible after symptoms of a type I hypersensitivity response to an allergen or asthmatic response appear. The DHEA derivative is administered in a manner which insures a systemic administration so that the blood levels of the active agent are quickly raised. Suitable modes of administration include intravenous, intramuscular, intranasal, intraocular, inhalant, aerosol or peritoneal. In addition, a patch which permits rapid uptake of the active agent can be used. The DHEA derivative is administered to patients in other pharmaceutically acceptable form and within binders, elixirs or other pharmaceutically acceptable mixtures, or with other pharmaceutically acceptable carriers.

Pharmaceutical compositions containing a compound of the present invention as the active ingredient can be prepared according to conventional pharmaceutical compounding techniques. See, for example, *Remington's Pharmaceutical Sciences,* 18th Ed. (1990, Mack Publishing Co., Easton, Pa.). Typically, a therapeutically effective amount of the active ingredient will be admixed with a pharmaceutically acceptable carrier. The carrier may take a wide variety of forms depending on the form of preparation desired for administration, e.g., intravenous, intramuscular, intranasal, intraocular, inhalant, or parenteral.

For parenteral administration, the compound may dissolved in a pharmaceutical carrier and administered as either a solution of a suspension. Illustrative of suitable carriers are water, saline, dextrose solutions, fructose solutions, ethanol, or oils of animal, vegetative or synthetic origin. The carrier may also contain other ingredients, for example, preservatives, suspending agents, solubilizing agents, buffers and the like.

The dose of the DHEA derivative is based on well known pharmaceutically acceptable principles to deliver a DHEA equivalent dose of, e.g., 0.1–100 mg/kg, preferably 1–50 mg/kg, more preferably 2–20 mg/kg. Generally the dose of DHEA derivative necessary to deliver this level of DHEA dose or DHEA eqivalent dose is 1–1000 mg/kg, preferably 2–500 mg/kg, more preferably 2–200 mg/kg. The dose of DHEA derivative can be readily determined using conventional methods and will generally be in the range of the doses previously specified. For unprotected compounds, i.e., those which can be sulfated by human sulfotransferases or sulfatases, it is preferred to administer an excess dose to insure that sufficient active agent is administered, especially if sulfatases are not active at the site of tissue injury.

Several treatment protocols can be used for reducing mast cell derived allergic reactions. In one embodiment, a bolus of a DHEA derivative is administered and allowed to clear from the system. Up to six additional treatments can be made over a 24 hour period. In a second embodiment, a bolus of a DHEA derivative is administered followed by infusion a DHEA derivative. The infusion occurs over a period of 1 hour and contains half the dose specified above. The DHEA derivative is allowed to clear the system, and up to six additional treatments can be made over a 24 hour period. In addition, any combinations of these protocols can be used. If the treatment is for a type I hypersensitivity response to an allergen, the preferred modes of delivery are an inhalant, aerosol, intrasal or intraocular, depending on the symptoms and the severity of the response. If the treatment is for asthma, the preferred modes of delivery are an inhalant, aerosol, intravenous and intramuscular.

The present invention is described by reference to the following Examples, which are offered by way of illustration and are not intended to limit the invention in any manner. Standard techniques well known in the art or the techniques specifically described below were utilized.

EXAMPLE 1

Effect of DHEA on Reperfusion Injury

Male Sprague-Dawley rats weighing 130–170 g were randomly assigned to no pre-treatment, vehicle pre-treatment or DHEA pre-treatment (4 mg/kg). Animals were treated with vehicle or DHEA the day before and the day of surgery. Anesthesia was induced with intraperitoneal pentobarbital (60–70 mg/kg). The rats were placed on a heating pad, and body temperature (measured by rectal probe) was maintained at between 35°–37° C. Detection of the cremaster muscle on its neurovascular pedicle was performed according to conventional techniques (78–80). Briefly, a skin incision is made from the anterior iliac spine to the tip of the scrotum. The testis with cremaster muscle intact is then dissected away from the scrotum. An opening of 1 cm is made on the ventral surface of the cremaster, and the testis and spermatic cord are removed. Under a microscope, the neurovascular pedicle, consisting of the pubic-epigastric arteries, vein, and genitofemoral nerve, is then completely isolated by dissecting to the origin of the vessels from the external iliac artery and vein. Finally, the front wall of the cremaster muscle sac is opened and the island cremaster muscle flap is prepared for intravital videomicroscopy. The rat is secured on a specially designed tissue bath, and the cremaster muscle flap is spread over the coverglass in the opening at the bottom of the bath and fixed with 5-0 silk sutures. It is then transilluminated from below, using a fiberoptic tungsten lamp. The muscle is kept moist and covered with impermeable plastic film. The tissue bath, designed specifically for temperature control, is filled with 0.9% saline and the temperature maintained at between 35° C.–36° C. The microscope is equipped with a color video camera. The video image of the microcirculation is displayed on a 19" monitor, where the final magnification is ×1800. Measurement of microvascular activity is recorded after isolation of the muscle to establish the pre-ischemia baseline. After proper positioning of clamps to completely shut down blood flow to the muscle flap, the duration of the ischemic period is six hours. Following removal of clamps to induce reperfusion injury, activity in the microvasculature is measured at 30, 60 and 90 minutes post-reperfusion. In all experimental subjects, ischemia is followed by reflow and then by an initial period of flow of blood through the microcirculation. This burst of circulatory activity is followed by marked reperfusion injury that induces loss of flow.

The following parameters are used to evaluate the state of the cremaster muscle microvasculatory system prior to ischemia and after reperfusion.

Figure 1B:
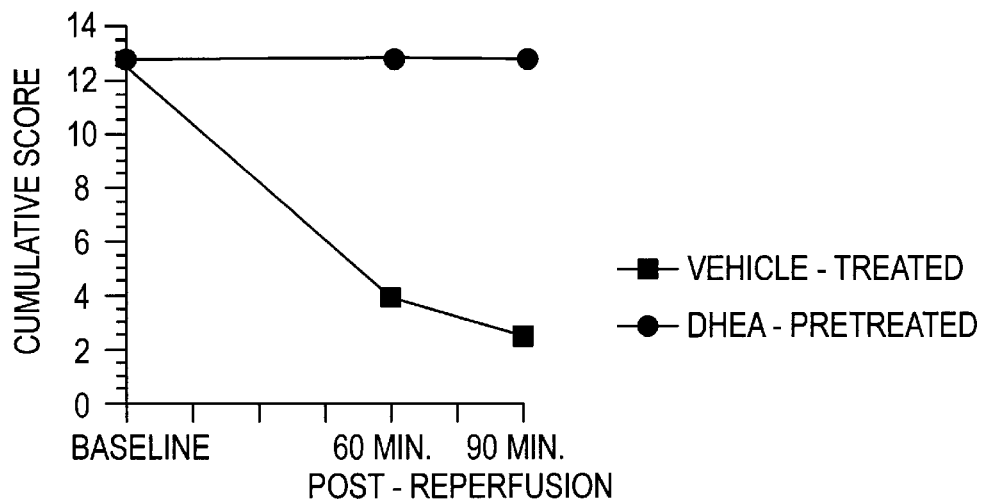
FIG. 1B shows the number of flowing capillaries in proximity to post-capillary venule in Zone 2 during reperfusion injury.
Figure 1C:
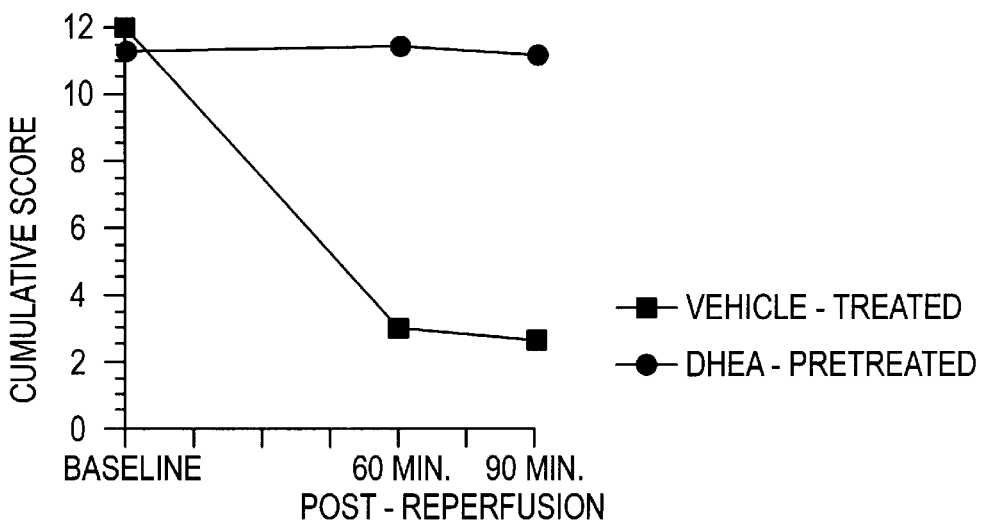
FIG. 1C shows the number of flowing capillaries in proximity to post-capillary venule in Zone 3 during reperfusion injury.

1) Density of Perfused Capillaries. The density of perfused capillaries in each of three flap regions (Zone 1, 2 and 3) is measured by counting the number of flowing capillaries in proximity to the preselected post-capillary venule. Nine visual fields of capillaries are counted at each postcapillary venule site, for a total of 27 fields per cremaster muscle flap. Results are shown in FIGS. 1A, 1B and 1C for Zones 1, 2 and 3, respectively.

Figure 2A:
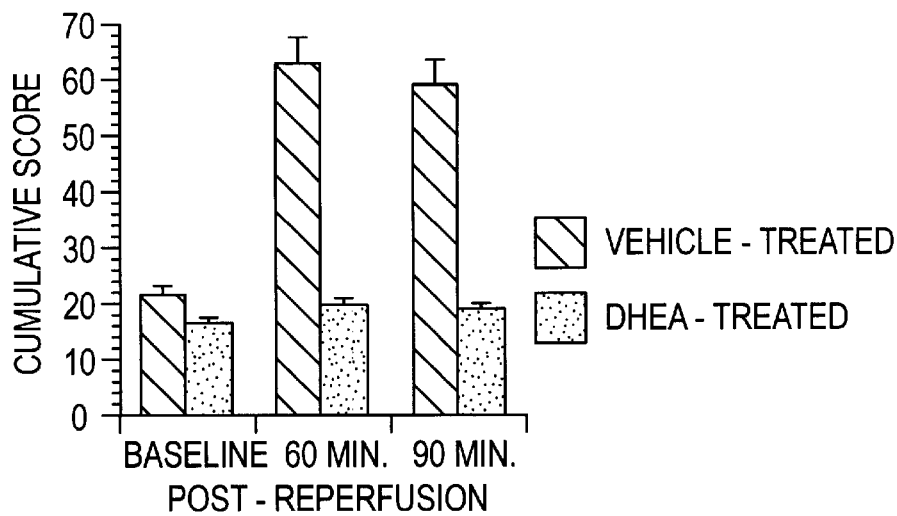
FIG. 2A shows the number of leukocytes rolling through the lumen of post-capillary venules in a two-minute period.
Figure 2B:
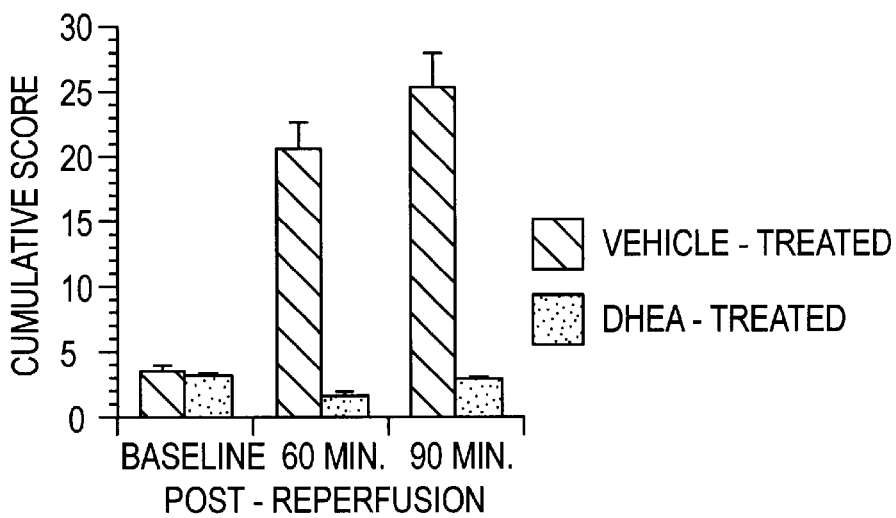
FIG. 2B shows the number of leukocytes adhering or sticking to the lumen of post-capillary venules in a two-minute period.
Figure 2C:
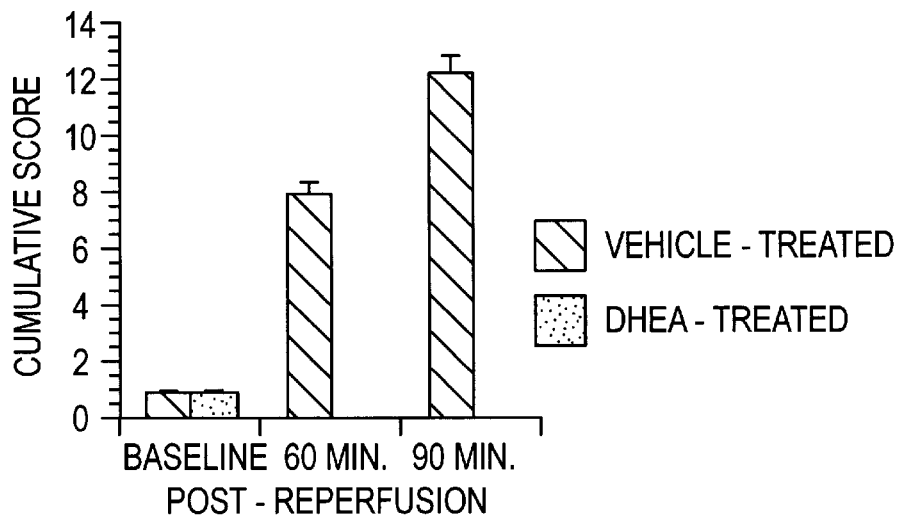
FIG. 2C shows the number of leukocytes migrating across the endothelium in a two-minute period.

2) Leukocyte Count in Postcapillary Venules. Video scans of three pre-selected post-capillary venules are taken in proximal, middle and distal flap regions. For each venule, the number of leukocytes rolling through the lumen, the number adhering to the endothelium and the number having migrated across the endothelium over a two-minute period are recorded. Results are shown in FIGS. 2A, 2B and 2C for rollers, strikers and diapedesis, respectively.

Figure 3A:
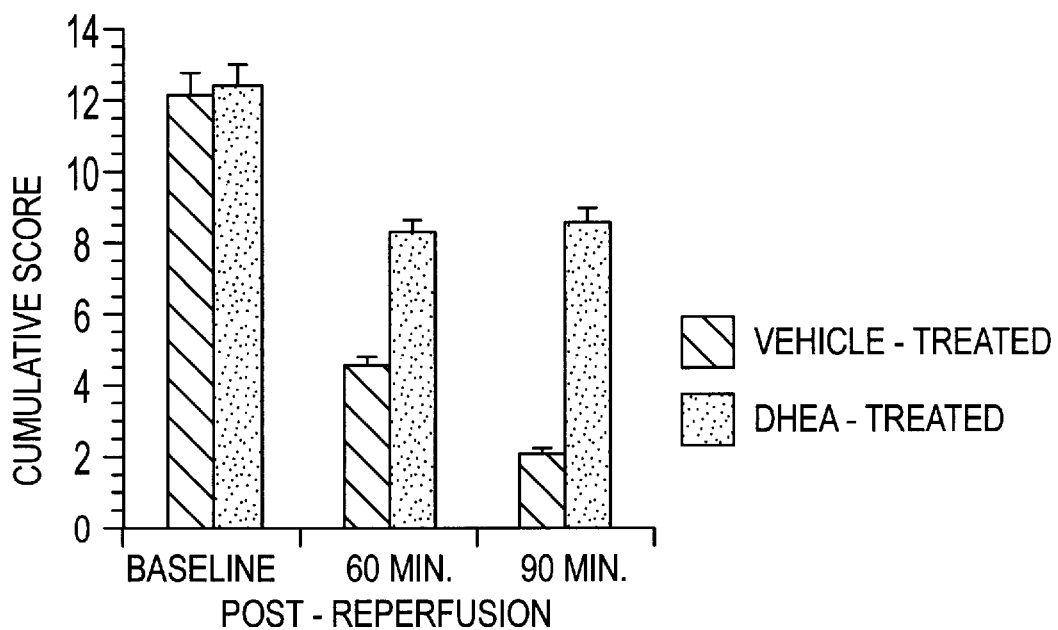
FIG. 3A shows red cell velocity of venous blood post-reperfusion.
Figure 3B:
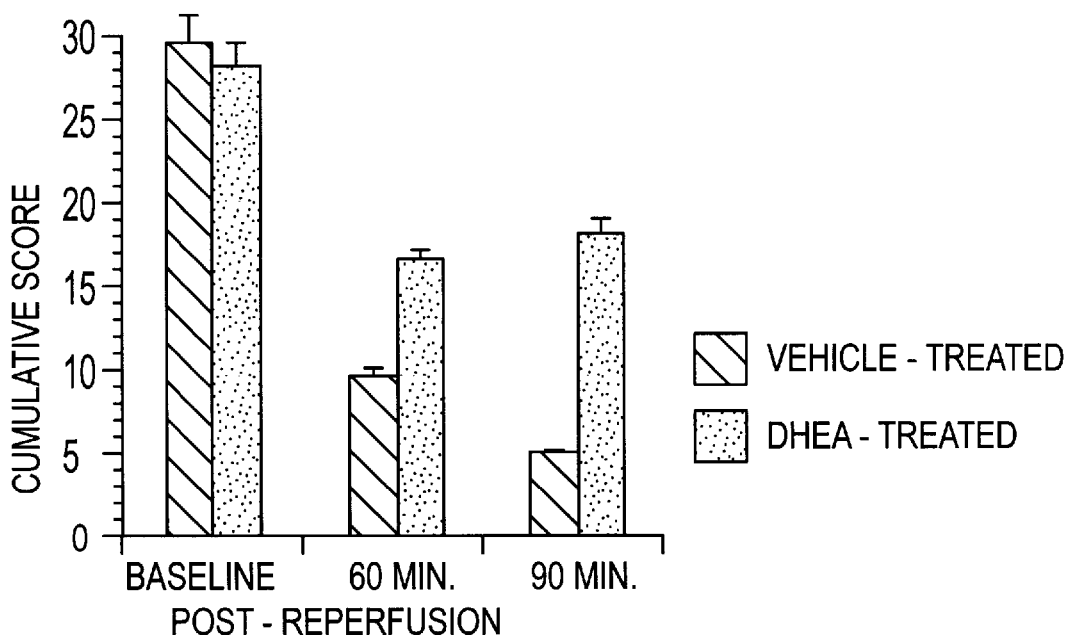
FIG. 3B shows red cell velocity of arterial blood post-reperfusion.

3) Red Blood Cell Velocities in A1 (First Order) and A2 (Second Order) Arterioles. Red blood cell velocities are recorded in the main arterioles of the cremaster flap using a custom-made optical Doppler velocimeter. Results are shown in FIGS. 3A and 3B, for velocity of venous and arterial blood, respectively.

A. Reperfusion Injury in Untreated and Vehicle-Treated Rats

Six rats were untreated and six rats were pre-treated with vehicle. Under conditions of six hours of ischemia and 90 minutes of reperfusion, the absolute number of rolling, sticking and transmigrated leukocytes increased dramatically within 60 minutes of reperfusion and showed a further increase at 90 minutes (FIGS. 2A–2C). A dramatic decrease was observed in the absolute number of perfused capillaries per high-powered field that were at both 30 and 60 minutes post-reperfusion, with a continued decrease in numbers of flowing capillaries at 90 minutes post-reperfusion (FIGS. 1A–1C). Likewise, red cell velocities in A2-sized vessels were significantly slower at 60 and 90 minutes post-reperfusion (FIGS. 3A and 3B).

B. Reperfusion Injury in DHEA-Treated Rats

Under conditions where rats were pre-treated with 4 mg/kg DHEA by subcutaneous injection the day before and the day of surgery, a marked and highly significant protective effect of the therapy was measured. All three parameters exhibited values that were close to, or identical with normal values. Of major importance, it was noted that all timepoints, endothelial-adherent properties were unchanged from baseline values. This conclusion is based on the fact that numbers of rolling, sticking and transmigrating leukocytes appeared remarkably similar to baseline values (FIGS. 2A–2C). Red cell velocities in A2 arterioles were slower to return to normal rates of flow, with velocities in some areas measuring 75% of normal at 90 minutes post-reperfusion (FIGS. 3A and 3B). At the 90-minute timepoint, the number of capillaries flowing in the microvasculature were not significantly different from the baseline values obtained prior to ischemia (FIGS. 1A–1C).

When DHEAS is substituted for DHEA at a dose 1.5 times that of the DHEA used, similar results are obtained. Similar results are obtained for the DHEA derivatives described above.

Without being bound by any theory of the physiological and biochemical operation of the DHEA congeners, it is believed that the anti-ischemic effects of these compounds are due to their activity on the adhesion of neutrophils to endothelial cells. Thus, these compounds are effective in preventing or reducing ischemia which may result from other types of tissue injury, which can be modulated by affecting adhesion to endothelial cells. This inhibition of neutrophil adhesion prevents activation of neutrophils and transmigration to the tissue side of the endothelium. Since transmigration of neutrophils is inhibited, neutrophil-induced massive damage to endothelial cells and parenchymal cells is prevented. Since neutrophil activation is prevented, production of cellular factors (by neutrophils) which leads to platelet aggregation is also prevented. Thus, progressive tissue necrosis is prevented or reduced. In addition, the progressive ischemia of gut tissue (leading to bacterial translocation) and of the epidermis and of cardiac muscle and the ischemia of the alveolar wall (leading to ARDS) are mediated through similar mechanisms. Thus, these compounds are also effective in preventing or reducing bacterial translocation and ARDS.

EXAMPLE 2

Effect of DHEA on Expression of P-Selectin by Platelets

Platelets were fractionated from freshly drawn blood (mature adults and elderly). Platelets were either utilized unwashed or washed. Washed platelets were obtained by conventional procedures (81, 82). Briefly, blood was collected to a syringe containing 1 volume of anticoagulant (0.085M sodium citrate, 0.065M citric acid, 2% dextrose) to 7 volumes of blood. Routinely, 50 ml of blood was withdrawn, Blood samples were centrifuged at 180×g for 15 minutes at room temperature to sediment red and white blood cells. The upper two-thirds of the platelet-rich plasma supernatant was carefully removed by aspiration, and the platelets were pelleted by centrifugation at 1100×g for 10 minutes at room temperature. The supernatant was decanted and the platelets were resuspended by gently mixing the sample in 2 ml of washing buffer (Tyrode's buffer without calcium, pH 6.50 at 37° C.). The platelet suspension was then diluted to a volume equal to the original volume of blood drawn with Tyrode's buffer, and centrifuged at 1100×g for 10 minutes at room temperature. The platelets were washed twice more by centrifugation and resuspended in 5 ml of incubation buffer (washing buffer adjusted to pH 7.4 at 37° C.). The platelets were counted in a Neubauer hemocytometer.

Washed and unwashed platelets were examined for the presence of P-selectin by direct immunostaining. Platelets ($1\times10^6$) were incubated with phycoerythrin-conjugated either negative control antibody or anti-human P-selectin monoclonal antibody (CD62 antibody, CAMFolio, Becton-Dickinson) for 15 minutes on ice. After that time, samples were washed twice with staining buffer (PBS, 0.1% sodium azide, 2% fetal bovine serum), reconstituted in 500 $\mu$l of staining buffer and analyzed by a FACScan flow cytometer (Becton Dickinson). The fluorescence was displayed as a single parameter histogram on a linear scale.

Measurement of P-selectin levels on surface of washed platelets obtained from blood of mature individuals showed that approximately 50% of washed platelets (resting platelets) tested positive for the presence of P-selectin. Sixty-eight percent of the unwashed platelets obtained from blood of an elderly individual tested positive for P-selectin. When whole blood form this individual was supplemented with 10 $\mu$M final concentration of DHEA prior to fractionation of the platelets and then test, only 12% of the platelets stained positive for P-selectin. This down-regulation of P-selectin by DHEA was accompanied by a 40% reduction in thrombin activated platelet aggregation. When this latter individual was placed on a supplemental therapy with DHEAS and the platelets fractioned from blood drawn during the supplemental therapy with DHEAS, the platelets were refractory to exogenous DHEA when activated with the same amount of thrombin as activated prior to the therapy. Thus, the observed down-regulation of P-selectin on the surface of platelets from elderly individuals by DHEA was accompanied by a prevention of thrombin-stimulated aggregation of these platelets by DHEA.

When DHEAS is used in place of DHEA at 1.5 times the DHEA dose, similar results are obtained. Similar results are obtained for the DHEA derivatives described above.

EXAMPLE 3

Effect of DHEA on Expression of P-Selectin by Endothelial Cells

Non-virally transformed Human Dermal Microvascular Endothelial cells were cultured using conventional techniques. Cells in passage number 2 were put on cover slips covered with attachment factor, and were grown in serum free system without phebol red until they became confluent. Groups of cells were incubated with vehicle alone or with 1 $\mu$M, 10 $\mu$M, 25 $\mu$M, 50 $\mu$M or 100 $\mu$M DHEA at 37° C. for 10 minutes. The cells were then activated with $10^{-5}$M histamine or with Dulbecco's phosphate buffer saline (dPBS) at 37° C. for 5 minutes.

The cells were then examined by indirect immunostaining/fluorescence microscopy. Briefly the cells were first washed 2–3 times in dPBS containing 1% bovine serum albumin (BSA), 1–2 minutes per wash. The cells were then fixed in ice-cold methanol for 5–7 minutes and then washed 2–3 times in dPBS containing 1% BSA and 0.01% azide. The cells were then incubated with anti P-selectin antibody at 4° C. in a humified chamber for 30 minutes. The cells were then washed 2–3 times in dPBS containing 1% BSA at 4° C., 1–2 minutes per wash. The cells were then incubated an anti anti-body linked to P-phycoerytherin at 4° C for 30–40 minutes, after which the cells were washed 2–3 times in dPBS containing 1% BSA at 4° C, 1–2 minutes per wash. The slides are then mounted and and P-selectin expression on endothelium is examined in fluorescence microscopy using rhodamine filterset.

Similary results are noted as seen for P-selectin expression in platelets. Namely, DHEA at concentrations of 10 $\mu$M or greater prevented the up-regulation of P-selectin expression normally observed on endothelium in response to histamine. The endothelium incubated with DHEA prior to histamine activation looked similar to the control, non-activated endothelium.

When DHEAS is used in place of DHEA, similar results are obtained. Similar results are obtained for the DHEA derivatives described above.

EXAMPLE 4

Effect of DHEAS on Hemorrhagic Shock

CF-1 mice, age 6–8 months, were anesthetized using methoxyflurothane and prepared for abdominal surgery. To maintain the required surgical level of anesthesia, methoxyflurothane was used as needed in a nose cone apparatus. Each mouse was tested for the level of respiration, eye blink response and response to a skin pinch to ensure a level of anesthesia appropriate for surgery. The duration of abdominal surgery was approximately two hours, during which time 35–40% of the animal's blood volume is removed over a 30 minute period. The removal of blood in a controlled manner simulates the effect of hemorrhagic shock. A slow intravenous infusion of the removed blood and a 2× volume of resuscitation fluid (lactated Ringers solution) into a central vein was made. The resuscitation fluid was supplemented with either 2 mg DHEAS or the excipient as a placebo. The peritoneum and overlying skin were sutured separately. Animals were maintained at 38°–39° C. until recovery is complete. Under these conditions, most of the placebo-treated animals died within 24–48 hours. Four hours after surgery, a colony forming unit (CFU) assay for bacteria was performed and malondialdehyde in liver was assayed using conventional techniques. Briefly, mesenteric lymph nodes (MLN) were removed and cultured on blood agar plates and the number of CFUs counted following culturing. The liver was removed and the amount malondialdehyde was measured. The survival rate, CFUs and malondialdehyde results are shown in Table 2.

TABLE 1

| Treatment Group | Survival at 48 Hours | CFU at 4 Hours Post Surgery ($10^{\underline{o}}$/MLN cells) | Malondialdehyde in Liver in 4 Hours (mMol) |
|---|---|---|---|
| Sham | 15/15 | 0.8 | 0.035 |
| Vehicle-treated, shock/resuscitation | 1/15 | 12,020 | 0.226 |
| DHEAS-treated, shock/resuscitation | 13/15 | 7.14 | 0.076 |

When DHEA is used in place of DHEAS, similar results are obtained. Similar results are obtained for the DHEA derivatives described above.

EXAMPLE 5

Effect of DHEA on Hypoxia-Induced Pulmonary Vasoconstriction

Isolated perfused ferret lungs are an established animal model to study secondary pulmonary hypertension, and were used in this example. In brief, male ferrets were anesthetized i.p. with pentobarbital sodium and the chest was opened. Stainless steel cannulae were secured in the left atrium and pulmonary artery, and the pulmonary artery and the aorta were ligated. The lungs were perfused with a mixture of autologous blood and Krebs-Henseleit buffer in a circulating manner at a constant rate of 85 ml/min. The perfusion circuit included a perfusate reservoir, a roller perfusion pump, filter, and a heat exchanger. The perfusion system was made of tygon tubing used for connections and for passage through the perfusion pump. The temperture of the perfusate was kept between 37° and 38° C., the pH was maintained at 7.35 to 7.40 by adding sodium bicarbonate to the reservoir as needed. The venous reservoir was placed below the lowermost portion of the lung.

The lungs were ventilated with a hypoxic gas mixture of 5% $CO_2$, 4% $O_2$, and 91% $N_2$ via a tracheotomy with a Harvard animal respirator for 30 minutes. The animals were ventilated with a tidal volume of 30 ml, at a rate of 18 breaths/min. and with 2 cm $H_2O$ positive end-expiatory pressure. For measurements, pulmonary arterial, left atrial and tracheal pressures were monitored using Gould Statha P231D pressure transducers connected to the inflow circulation and recorded on a Grass polygraph. After 30 minutes of ventilation with hypoxic gas mixture, DHEA in a dose between 8–12 mg/kg body weight was added to reservoir, and perfusate was allowed to perfuse ferret lungs for 1.5 hours. A sudden drop to baseline level in pulmonary artery pressure was obserted upon DHEA delivery. Pulmonary artery pressure remained at basal level until the end of the experiment, i.e., a total of two hours. These results demonstrate the vasodilatory effect of DHEA in pulmonary circulation constricted in response to hypoxia. DHEA treatment lowered pulmonary pressure completely to normal, and this lowering of pressure was sustained. When compared with nitric oxide (a therapeutic agent conventionally used) in the same model, DHEA was more potent in reducing pulmonary artery pressure. The effect of nitric acid lasted for only minutes, whereas the effect of DHEA lasted for at least two hours. Similar results are obtained for the DHEA derivatives described above.

EXAMPLE 6

Bone Marrow-Derived Mast Cell Protocol

Mast cells are prepared by conventional techniquese (56–58). Briefly, the legs are removed from Balb/c mice, the meat is stripped away, and the marrow is flushed out with PBS using a 27 g needle. The cells are cultured in a mixture of 2/3 RPMI-1640+19% FBS and cells that secrete recombinant IL-3. The bone marrow cells are allowed to differentiate for 18–25 days in the IL-3-containing mixture before being used for experiments. Bone marrow cells cultured in this manner have been determined to have a phenotype similar to mucosal mast cells and are referred to as bone marrow-derived mast cells (BMMC).

Degranulation of the BMMC is measured spectrophotometrically following stimulation. Briefly, BMMC at a density of $10^7$ cells/mL in HBSS are incubated for 10 mins at room temperature with 100 $\mu$M DHEA, dissolved in DMSO or DMSO alone. The stimulant is then added and the cells are allowed to degranulate for 30 mins at 37 C. The cells are then centrifuged and the supernatant is collected. The supernatant is assayed in triplicate for glucoronidase activity by adding 100 $\mu$L of the supernatant to 150 $\mu$L of 0.5 mg/mL phenolphthalien-glucuronic acid in citrate buffer, pH 4.5. The reaction is allowed to proceed for 1.5 hrs at 37 C before being terminated by the addition of 250 $\mu$L of 0.4M glycine, pH 10.5. The absorbance of the samples is then read spectrophotometrically at 552 rm.

EXAMPLE 7

In vitro Degranulation of Cultured Murine Mast Cells Using ATP

Figure 4:
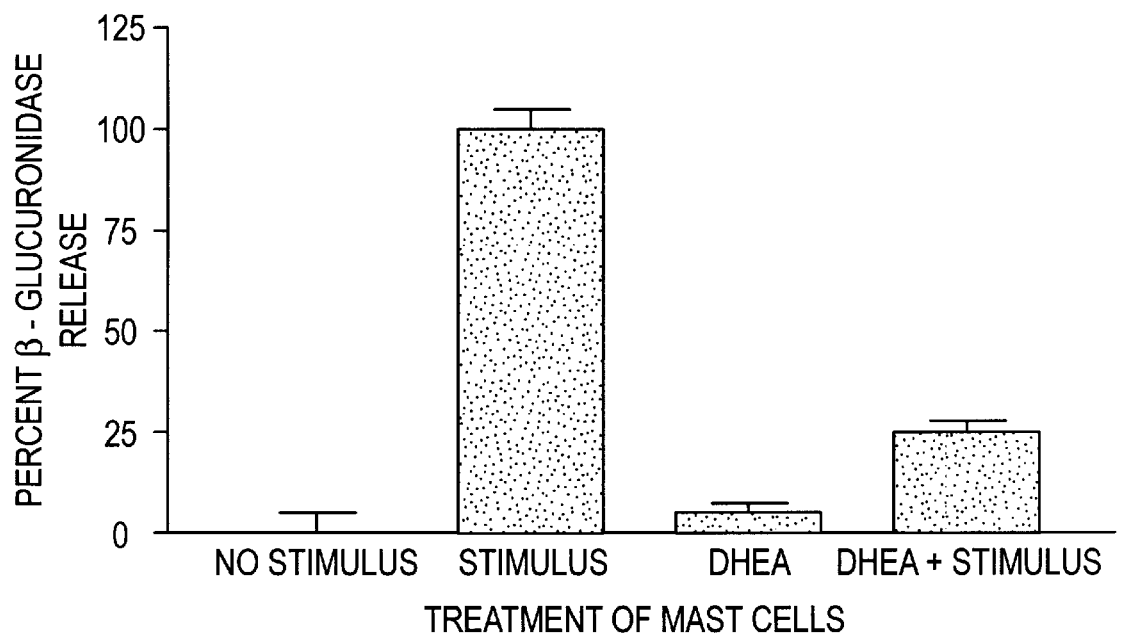
FIG. 4 shows that administration of DHEA inhibits ATP activation-induced degranulation of mast cells. Mast cells were harvested from propagation cultures and dispensed at $1 \times 10^7$ cells/ml. Cells were then exposed to either vehicle substance, 1 mM ATP, 100 $\mu$M DHEA or 100 $\mu$M DHEA prior to stimulation with 1 mM ATP. Culture supernatants were harvested 10 minutes after addition of the last test substance to quantitate the amount of β-glucuronidase, a product of mast cell degranulation. Viability of cell cultures remained above 90% during these tests.

A homogeneous population of mast cells was cultivated from murine bone marrow using accepted and well documented methodology as described above. The homogeneity of the in vitro-propagated mast cells was confirmed and verified by conventional flow cytometry techniques, staining for the Fc receptor of IgE. Between days 14 and 21 of propagation, mature mast cells were harvested and prepared for test cultures. The objective was to assess the effect of DHEA on mast cell stimulus-coupled degranulation. Prepared mast cells were dispensed into test culture wells at a density of $1 \times 10^7$ cells/ml. In some cultures, mast cells were induced to degranulate after addition of 100 $\mu$M ATP to the test culture. Parallel groups of mast cell cultures were preexposed to DHEA at various doses followed by activation with ATP. In the example of FIG. 4, there is no measurable degranulation of mast cells as measured by release of $\beta$-glucuronidase from cytosolic storage granules of the cells in the absence of the stimulus. Yet the introduction of 100 $\mu$M ATP to the cultures caused a significant release of $\beta$-glucuronidase. When mast cells were exposed to DHEA alone, there was no measurable degranulation. However mast cell cultures pre-exposed to doses of 100 $\mu$M DHEA 5 to 10 minutes prior to activation by ATP, exhibited approximately 80% inhibition of degranulation. Lower doses of DHEA typically show proportionately less capacity to inhibit degranulation.

EXAMPLE 8

Figure 5:
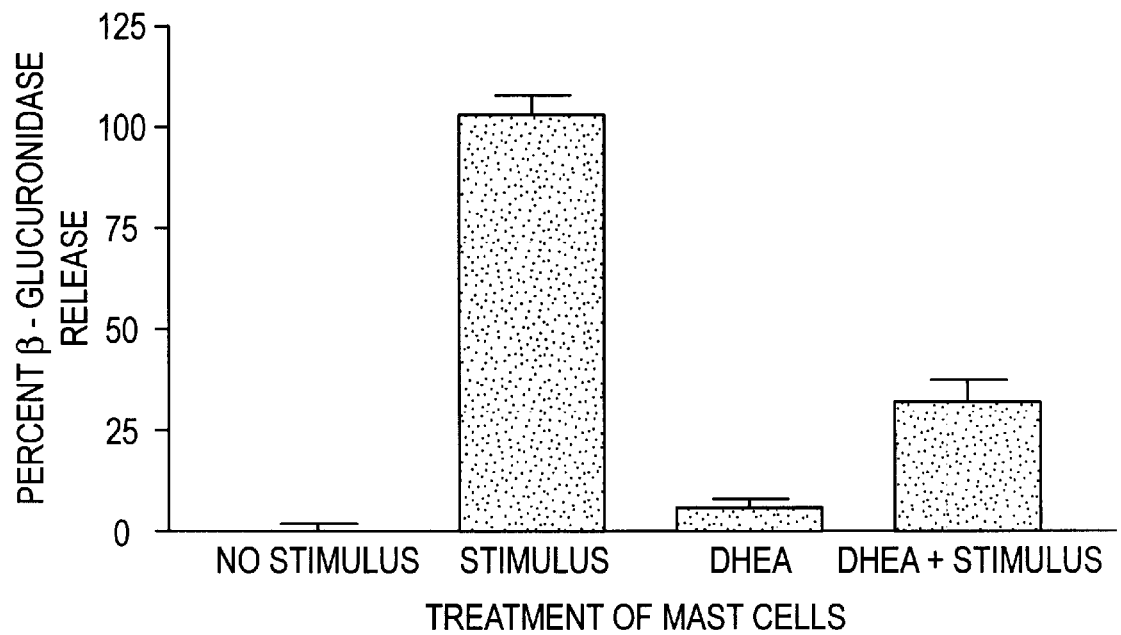
FIG. 5 shows that administration of DHEA inhibits IgE-antiIg-E complex activation-induced degranulation of mast cells. Mast cells were harvested from propagation cultures and dispensed at $1 \times 10^7$ cells/ml. Cells were then exposed to either vehicle substance, IgE-antiIg-E complex, 100 $\mu$M DHEA or 100 $\mu$M DHEA prior to stimulation with the Ig-E mixture. Culture supernatants were harvested 10 minutes after addition of the last test substance to quantitate the amount of β-glucuronidase, a product of mast cell degranulation. Viability of cell cultures remained above 90% during these tests.

In vitro Degranulation of Cultured Murine Mast Cells Using the Physiologic Stimulus Cross-linking of IgE Receptors A homogeneous population of mast cells was cultivated from murine bone marrow using accepted and well documented methodology as described above. The homogeneity of the in vitro propagated mast cells was confirmed and verified by conventional flow cytometry techniques, staining for cell-type specific markers to rule in and rule out other cell types. Between days 14 and 21 of propagation, mature mast cells were harvested and prepared for the test cultures. The objective was to assess of the effect of DHEA on mast cell stimulus-coupled degranulation. Prepared mast cells were dispensed into test culture wells at a density of $1 \times 10^7$ cells/ml. In some cultures, mast cells were induced to degranulate after cross linking of IgE receptors with IgE antigen-antibody complexes. In parallel groups of cultures mast cells were preexposed to DHEA at various doses followed by activation using anti-IgE antibody. In the example of FIG. 5, there is no detectable degranulation of mast cells as measured by release of $\beta$-glucuronidase from cytosolic storage granules of the cells in the absence of the stimulus. Yet the introduction of anti IgE receptor antibody to the cultures caused a significant release of $\beta$-glucuronidase. When mast cells were exposed to DHEA alone, there was no measurable degranulation. However, mast cells pre-exposed to doses of 100 $\mu$M DHEA 5 to 10 minutes prior to activation with anti-IgE antigen-antibody complexes, exhibited approximately 70% inhibition of degranulation at the 100 $\mu$M dose. Lower doses of DHEA showed proportionately less capacity to inhibit degranulation.

EXAMPLE 9

Figure 6:
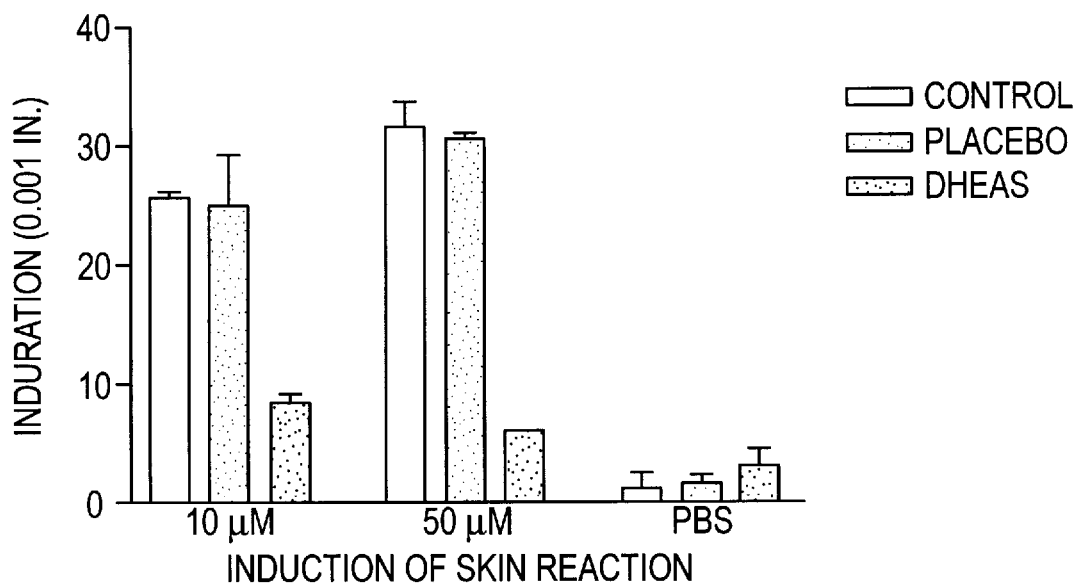
FIG. 6 shows that allergic reactions mediated by mast cells are prevented by exposure to DHEAS. Groups of age- and sex-matched Balb/c mice were given 12 mg/kg DHEAS, placebo, or saline by intravenous injection 90 minutes before induction of an allergic skin reaction. Mast cell resident in the skin were activated with either 10 $\mu$l of PBS, 10 $\mu$M ATP or 50 $\mu$M ATP. After another 45 minutes, mice were sacrifices and skin was prepared for measurement of induction.
Figure 7:
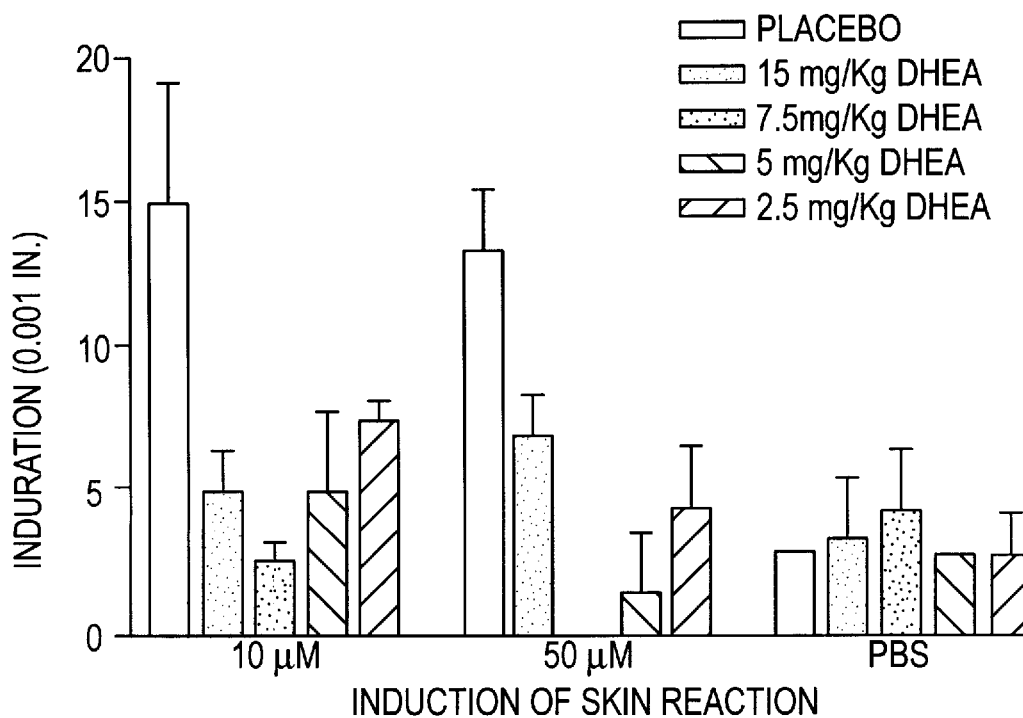
FIG. 7 shows that allergic reactions mediated by mast cells are prevented by exposure to DHEA. Groups of age- and sex-matched Balb/c mice were given 15, 7.5, 5 or 2.5 mg/kg DHEA or placebo substance 15 minutes before induction of an allergic skin reaction. Mast cell resident in the skin were activated with either 10 $\mu$l of PBS, 10 $\mu$M ATP or 50$\mu$M ATP. After another 45 minutes, mice were sacrifices and skin was prepared for measurement of induction.

In vivo Inhibition of Immediate Hypersensitivity Reactions by Administration of Either DHEAS or DHEA Immediate hypersensitivity reactions of the skin are easily elicited in experimental mice. The cutaneous model can serve as a basic tool to study drug candidates that regulate development and propagation of allergic reactions, as well as a basic model applicable to allergic reactions in general. The response in mice is induced through intradermal injection of substances that are known to activate mast cells. An experiment was designed to test the effect of DHEA on immediate hypersensitivity reaction in mice. To elicit an immediate inflammatory reaction, mice are given graded doses of ATP in a 10 $\mu$l volume delivered by high-precision syringes to the lateral, dorsal surface of mice (5 per group). Forty-five minutes after injection of the ATP stimulus, mice are sacrificed. Skin sections including both involved and uninvolved skin are excised, flattened and fixed in 10% buffered formalin for one week. Sections are trimmed to enable measurement of skin thickness in control (uninvolved skin) versus ATP (involved skin). In FIG. 6, it is shown that intradermal injection of either 10 or 50 μg ATP elicited a dose-dependent inflammatory reaction as measured by induration of skin at the site of injection (in 0.001 inch). There was litte to no induration caused by the intradermal injection of PBS at a third site on the back. To separate groups of age- and sex-matched mice, either 12 mg/kg DHEAS or a comparable volume of placebo substance was administered intravenously. Ninety minutes after administration of test articles, ATP was injected intradermally to elicit a hypersensitivity reaction. We observed that pre-exposure to DHEAS i.v. prior to induction of skin reactions caused a significant inhibition of the induration >80%. In FIG. 7, separate groups of age- and sex-matched mice were given doses of either 15, 7.5, 5 or 2.5 mg/kg DHEA or a comparable volume of placebo substance intravenously. Fifteen minutes after administration of test articles, ATP was injected intradermally to elicit a hypersensitivity reaction. We observed that pre-exposure to 5 and 7.5 mg/kg DHEA i.v. prior to induction of skin reactions caused a significant inhibition of the induration >80. Higher and lower doses caused less inhibition.

EXAMPLE 10

In vivo Immediate Hypersensitivity Reactions are Mast-Cell Dependent

An experiment was designed to test the dependence of ATP-mediated cutaneous immediate hypersensitivity reaction on mast cells in mice. The homozygous $WVB6F_1/J$-$W/W^v$ mast cell deficient and their heterozygous mast cell wild-type littermates (C57BL/6J-WV/W) were tested for cutaneous, immediate inflammatory reactions using ATP as the stimulus. Groups of 5 mice from each type are given graded doses of ATP in a 10 ill volume delivered by high-precision syringes to the lateral, dorsal surface of mice. Forty-five minutes after injection of the ATP stimulus, mice are sacrificed. Skin sections including both involved and uninvolved skin are excised, flattened and fixed in 10% buffered formalin for one week. Sections are trimmed to enable measurement of skin thickness in control (uninvolved skin) versus ATP (involved skin). The intradermal injection of either 10 or 50 μg ATP elicited a dose-dependent inflammatory reaction in the wild type littermates but no reaction was elicited in mast cell deficient mice. There was little to no induration caused by the intradermal injection of saline at a third site on the back.

EXAMPLE 11

Effect of Single Dose of DHEAS on the Magnitude of the Allergic Response to a Skin Challenge in Human Volunteers with a Proven Allergy Human volunteer's medical history is taken to determine whether he/she has a skin allergy. If this cannot be verified per the volunteer's medical records, the volunteer will be asked to undergo a skin allergy challenge. Only those volunteers with a confirmed skin allergy are enrolled into the study. For determining the acceptability of the volunteers for this study, they must be the following criteria:

Inclusion Criteria

Healthy volunteers with a demonstrable cutaneous allergy to a known allergen.

Free from significant disease as determined by history, physical examination and laboratory screens.

Available to complete the study.

Able to give informed consent.

Female volunteers must not be of child-bearing potential, having been surgically sterilized at least 6 months prior to her participation in the study, or post-menopausal as evidenced by the absence of menses for a minimum of 12 months prior to her participation in the study.

Exclusion Criteria

Participation in an investigational drug study in the previous 4 months.

Volunteers who have donated 450 mL or more blood in the previous 3 months, or who intend to donate blood within 3 months after his/her participation in the study.

Volunteers who have received a regular course of medication during the 4 weeks prior to his/her participation in the study.

Volunteers with a history of alcohol or drug abuse, or a positive test for one or more drugs in the urine drug screen.

Volunteers who regularly drink more than 21 units of alcohol per week.

Volunteers who smoke more than 10 cigarettes per day.

Body Mass Index outside the range 21–32 inclusive.

Volunteers who test positive for hepatitis B surface antigen.

Volunteers receiving antihistamines, steroids, anti-inflammatory drugs or any immunomodulator.

Volunteers with a history of anaphylaxis.

The volunteer has a history of malignancy within the past five years, with the exception of a successfully resected basal cell carcinoma.

The volunteer has any clinically significant condition or illness which, in the opinion of the Investigator, would affect the safety, pharmacokinetc or clinical assessments The volunteer has a history of polycythemia.

At screening, a standardized skin allergy challenge is performed, including a positive and a negative control. The dimensions of the wheals are measured, recorded and photographed at 30 minutes post-challenge, two hours post-challenge.

Volunteers are admitted to the Phase 1 Unit at approximately 1800 hrs (6 p.m.) on the evening prior to each dosing period. Each volunteer is queried regarding any adverse experiences and medication taken since his/her screening. Continuous Holter ECG monitoring is initiated on the evening of admission and continue until discharge at approximately 24 hours post-dose.

Prior to administration of the first dose of the test drug (12 mg/kg DHEAS or placebo), a cannula is inserted into a forearm vein of the volunteer in order to facilitate venous blood sampling. Blood samples (10 mL each) are drawn prior to administration with the test drug. The blood samples are used to conduct laboratory safety testing (hematology and chemistry) and pharmacokinetic analyses. The first one milliliter (1 mL) of blood taken from the cannula at each sampling is discarded. After each sampling, the cannula is flushed with 2 mL of 0.9% Sodium Chloride for Injection.

A second cannula is inserted into a suitable forearm vein in the volunteer's other arm. This cannula is used only for administration of the test drug (DHEAS or placebo), and it is removed upon completion of the infusion. The test drug is infused over a period of at least 30 minutes. It is mixed with 250 mL of 5% Dextrose for Injection prior to infusion. The volunteers lie on their beds in a semi-recumbent position during the infusion of the test drug.

Pharmacokinetic blood samples (10 mL each) are withdrawn at the following time points: Pre-dose, 15, 30, 45, 60

(1 hour), 90, 120 (2 hours), 150, 180 (3 hours) and 240 minutes (4 hours) after completion of the infusion. Blood pressure is measured and recorded at pre-dose, every 10 minutes after start of infusion of the test drug until one (1) hour after completion of the infusion, and then hourly until six (6) hours after completion of the infusion.

A skin allergy challenge ( as conducted during screening) is performed at 60 minutes after completion of infusion of the test drug (DHEAS or placebo). The skin test site is examined, measured, assessed and photographed at 30 minutes and at 2 hours post-challenge.

A blood sample (10 mL) is drawn 24 hours post-dose. The sample is used to conduct laboratory safety (hematology and chemistry) testing and a pharmacokinetic analysis. Holter ECG monitoring is discontinued and, at the discretion of the Investigator, the volunteer may be discharged from the Phase 1 Unit.

Within the time period 10–14 days following administration of the first dose of test drug, the volunteer returns to the Phase 1 Unit to receive his/her second dose of the test drug. The procedures and evaluations as described above are repeated. In addition, flow cytometry measurements are made During the period 5–10 days following administration of the second dose of the test drug, the volunteer will return to the Phase 1 Unit for a safety follow-up evaluation.

The administration of DHEAS in this study is seen to reduce the allergic reaction as measured by the size of the wheals post-challenge with the allergen.

EXAMPLE 12

Effect of a Single Dose of DHEAS on Excerise Induced Asthma in Human Volunteers

Human volunteer's medical history is taken to determine whether he/she has a history of exercise-induced asthma. The volunteer will be asked to undergo a cold air challenge with exercise. Only those volunteers with a reduction in forced vital capacity (PVC) and forced expired volume (FEV) of at least 17% from pre-challenge baseline are enrolled into the study. For determining the acceptability of the volunteers for this study, they must be the following criteria:

Inclusion Criteria

Healthy volunteers with a demonstrable history of exercise-induced asthma.

Free from significant disease as determined by history, physical examination and laboratory screens.

Available to complete the study.

Able to give informed consent.

Female volunteers must not be of child bearing potential, having been surgically sterilised at least 6 months prior to the study, or post-menopausal as evidenced by absence of menses for a minimum of 12 months prior to the study.

Exclusion Criteria

Participation in an investigational drug study in the previous 4 months.

Volunteers who have donated 450 ml or more blood in the previous 3 months, or who intend to donate blood within 3 months of the end of the study.

Volunteers who have received a regular course of medication during the 4 weeks prior to the study.

Volunteers with a history of alcohol or drug abuse. Positive test for one or more drugs in the urine drug screen.

Volunteers who regularly drink more than 21 units of alcohol per week.

Volunteers who smoke cigarettes or have smoked in the 6 months prior to the study.

Body Mass Index outside the range 21–32 inclusive.

Volunteers who test positive for hepatitis B surface antigen.

Volunteers receiving antihistamines, steroids, anti-inflammatory drugs or any immunomodulator. Volunteers who take inhaled beta agonists on an as required basis are eligible for the study.

Volunteers with a history of anaphylaxis.

The volunteer has any clinically significant condition or illness which, in the opinion of the Investigator, would affect the safety, pharmacokinetic or clinical assessments.

The volunteer has a history of polycythemia.

A volunteer undergoes the designated screening procedures within four (4) weeks prior to his/her participation in the study. During Screening, the volunteer undergoes the following procedures: (a) medical history taken; (b) complete physical examination, including vital signs; (c) cold air challenge with exercise [on a treadmill according to a standard protocol (level 1: Bruce grade 2–2 minutes; level 2: Bruce grade 3 –2 minutes; level 3: Bruce grade 5–6 minutes) while breating cold air (4° C. and dry air from a generator]; (d) blood samples (15 mL) withdrawn for hematology, chemistry and Hepatitis B surface antigen test; (e) urinalysis, including a screen for drugs of abuse; and (f) verification of qualification versus the inclusion/exclusion criteria.

One day prior to administration of the test drug on Test Drug Day 1, on Test Drug Day 2 and on Test Drug Day 3, volunteers are admitted to the Phase 1 Unit at approximately 1800 hrs on the evening prior to each dosing period. Each volunteer is questioned regarding any adverse experiences and medication taken since his/her Screening. Continuous Holter ECG monitoring is initiated on the evening of admission and continue until discharge at approximately 24 hours post-dose.

Prior to administration of the first dose of the test drug (12 mg/kg DHEAS or placebo), a cannula is inserted into a forearm vein of the volunteer in order to facilitate venous blood sampling. Blood samples are drawn prior to administration with the test drug. The blood samples are used to conduct laboratory safety testing (hematology and chemistry), cytokine assay, flow cytometry and pharmacokinetic analyses. The first one milliliter (1 mL) of blood taken from the cannula at each sampling is discarded. After each sampling, the cannula is flushed with 2 mL of 0.9% Sodium Chloride for Injection.

A second cannula is inserted into a suitable forearm vein in the volunteer's other arm. This cannula is used only for administration of the test drug (DHEAS or placebo), and it is removed upon completion of the infusion. The test drug is infused over a period of at least 30 minutes. It is mixed with 250 mL of Dextrose for Injection prior to infusion. The volunteers lie on their beds in a semi-recumbent position during the infusion of the test drug.

Pharmacokinetic blood samples (10 mL each) are withdrawn at the following time points: Pre-dose, 15, 30, 45, 60 (1 hour), 90, 120 (2 hours), 150, 180 (3 hours), 240 minutes (4 hours) and 24 hours after completion of the infusion. Blood pressure is measured and recorded at pre-dose, every 10 minutes after start of infusion of the test drug until one (1) hour after completion of the infusion, and then hourly until six (6) hours after completion of the infusion. Additional blood pressure recordings is made during the period of cold air/exercise challenge.

At approximately 45 minutes after completion of the infusion of the test drug, the volunteer is taken to the Cardio-Analytics laboratory, where pre-exercise flow volume loops is recorded. After the 60 minute post-dose blood sample has been obtained, a cold air challenge with exercise as described above is conducted.

On Day 2 (the first day following the first administration of the test drug), blood samples are drawn 24 hours post-dose. The sample is used to conduct laboratory safety (hematology and chemistry) testing and a pharmacokinetic analysis. Holter ECG monitoring is discontinued and, at the discretion of the Investigator. the volunteer may be discharged from the Phase 1 Unit.

On Days 10–14 (includes the day of the second administration of the test drug), within the time period 10–14 days following administration of the first dose of test drug, the volunteer returns to the Phase 1 Unit to receive his/her second dose of the test drug. The procedures and evaluations as described above are repeated.

During the period 5–10 days following administration of the second dose of the test drug, the volunteer returns to the Phase 1 Unit for a safety follow-up evaluation. The follow-up includes: complete physical examination, including vital signs; ECG; hematology and chemistry testing; and urinalysis.

The administration of DHEAS in this study is seen to reduce the asthmatic symptoms.

It will be appreciated that the methods and compositions of the instant invention can be incorporated in the form of a variety of embodiments, only a few of which are disclosed herein. It will be apparent to the artisan that other embodiments exist and do not depart from the spirit of the invention. Thus, the described embodiments are illustrative and should not be construed as restrictive.

LIST OF REFERENCES (1) De Peretti, E. et al. (1978). *J. Clin. Endocrinol. Metab.* 47:572.
(2) Swartz, A. G. et al. (1981). *Nutr. Cancer* 3:46.
(3) Yen, T. T. et al. (1977). *Lipids* 12:409.
(4) Coleman, D. C. (1982). *Diabetes* 31:830 (1982).
(5) Flood, J. F. (1988). *Brain Res.* 447:269
(6) Daynes, R. A. et al. (1990). *Eur. J. Immunol.* 19:2319.
(7) Morehouse, J. L. et al. (1986). *Gastroenterol* 91:673–682.
(8) Maejimak, et al. (1984). *Arch. Surg.* 119:166–172.
(9) Czaja, A. J. et al. (1974). *N. Engl. J. Med.* 291:925–929
(10) Seavitt, S. (1967). *Br. J. Sure* 54:32–41.
(11) Desai, M. H. et al. (1991). *Surgery Gyn. Obstet.* 172:257–261.
(12) Deitch, E. A. and R. Berg (1987). *J. Burn Rehab.* 8:475–482.
(13) Simon, R. H. and Ward, P. A. (1992). In *Inflammation: Basic, Principles and Clinical Correlates,* 2d Ed., Galin, J. I. et al., Eds., Raven Press, Ltd., New York, pp. 999–1016.
(14) (1979). *N. Engl. J. Med.* 300:213.
(15) (1973). *Med. Clin. North Am.* 57:637.
(16) (1976). *Am. Rev. Resp. Dis.* 114:775.
(17) (1980). *Ann. Intern. Med.* 93:391.
(18) (1981). *Lancet* 1:681.
(19) Madden, J. A. et al. (1985). *J. Appl. Physiol.* 59:113.
(20) Hoshino, Y. et al. (1988). 65:2468.
(21) Bergofsky, E. H. et al. (1967). 20:506.
(22) Harder, D. (1985). *J. Appl. Physiol.* 59:1389.
(23) McMurty, I. F. et al. (1976). *Circul. Res.* 38:99.
(24) Sturani, C. et al. (1983). *Chest* 84:135.
(25) Voelkel, N. F. et al. (1981). *J. Clin. Invest.* 67:238.
(26) Farrukh, I. S. et al. (1992). *Am. Rev. Resp. Dis.* 145:1389.
(27) Nelson, C. et al. (1988). *The national ambulatory health care survey, United States,* 1975–1981 *and* 1985 *trends,* Washington, D.C.; Vital and Health Statistics, U.S. Dept. of Human Services publication (PHS) 88–1754, Series 13, No. 93.
(28) Coombs, R. R. A., et al. (1975). In: *Clinical aspects of immunology, third ed.,* Gell, P. G. H., Coombs, R. R. A., Lachmann, P. J., eds., Oxford; Blackwell Scientific, pp. 761–78
(29) Steinberg, P. et al. (1974). *J. Allergy Clin. Immunol.* 54:359–366.
(30) O'Hehir, R. E. et al.. (1991). *Adv. Immunol.* 9:67–95.
(31) Higgins, J. A. et al. (1992). *J. Allergy Clin. Immunol.* 90:749–756.
(32) Marsh, D. G. et al. (1988). In: *Immunol. Diseases, 4th ed.,* Samter, M., Talmade, D. W., Frank, M. M., Austen, K. F., Claman, H. N., eds., Boston; Little, Brown, pp. 981–1008.
(33) Smith, P. L. et al. (1980). *J. Clin. Invest.* 66:1072–1080.
(34) Naclerio, R. M. et al (1983). *Am. Rev. Respir. Dis.* 128:597–602.
(35) Holgate, S. T. et al. (1988). In: *Allergy, principles and practice, 3rd ed.,* Middleton, E., Reed, C. E., Ellis, E. F., Adkinson, N. F. Jr., Yunginger, J. W., eds., St. Louis; C. V. Mosby, pp. 135–163.
(36) Gordon, J. R. et al. (1991). *J. Exp. Med.* 174:103–107.
(37) Duff, A. L. et al. (1992). *Pediatr. Clin. North Am.,* 39:1227–1291.
(38) Busse, W. W. et al. (1988). In: *Allergy, principles and practice, 3rd.* ed., Middleton, E. Jr., Reed, C. E., Ellis, E. F., Adkinson, N. F. Jr., Yunginger, J. W. eds., St. Louis; C. V. Mosby, pp. 969–998.
(39) McFadden, E. R., Jr. et al. (1992). *N. Engl. J. Med.* 327:1928–1937.
(40) Gleich, G. J. (1990). *J. Allergy Clin. Immunol.* 85:422–436.
(41) Frew, A. J. et al. (1990). *J. Allergy Clin. Immunol.* 85:533–539.
(42) Duff, A. L. et al. (1992). *Pediatr. Clin. North Am.* 39:1277–1291.
(43) Gundel, R. H. et al. (1991) *J. Clin. Invest.* 87:1470–1473.
(44) Plaut, M. et al. (1986). *J. Allergy Clin. Immunol.* 78:968–973.
(45) Kaliner, M. et al. (1982). *Ann. Intern. Med.* 96:349–357.
(46) Casale, T. B. (1991). *J. Allergy Clin. Immunol.* 88:1–16.
(47) Ollerenshaw, S. et al. (1989). *N. Engl. J. Med.* 320:1244–1248.
(48) Stevenson, D. D. et al. (1988). In *Allergy, princoples and practice, 3rd ed.,* Middleton, E. Jr. et al, eds., St. Louis; C. V. Mosby, pp. 1537–1554.
(49) Pollart, S. M. et al. (1989). *J. Allergy Clin. Immunol.* 83:875–882.
(50) Platts-Mills, T. A. E. et al. (1982). *Lancet* 2:675–678.
(51) Molfino, N. A. et al. (1991). *Lancet* 338:199–203.
(52) Koenig, J. Q. et al. (1989). *Environ. Health Perspect.* 79:173–178.
(53) Evans, D. et al. (1987). *Am. Rev. Respir. Dis.* 135:567–572.
(54) Weiss, K. B. et al. (1990). *JAM* 284:1683–1687.

(55) Gergen, P. J. et al. (1992). *Am. Rev. Respir. Dis.* 146:823–824.
(56) Smith, T. J. et al. (1994). *Eur. J. Immunol.* 24:822–826.
(57) Ducharme, L. A. and Weis, J. H. (1992). *Eur. J. Immunol.* 22:2603–2607.
(58) Gurrish, M. F. et al. (1992). *J. Immunol.* 149:1964–1972.

What is claimed is:

1. A method for reducing mast cell mediated allergic reactions in a patient in need thereof which comprises administering to said patient an effective amount of a dehydroepiandrosterone (DHEA) derivative having the general formulas I and II and their pharmaceutically acceptable salts

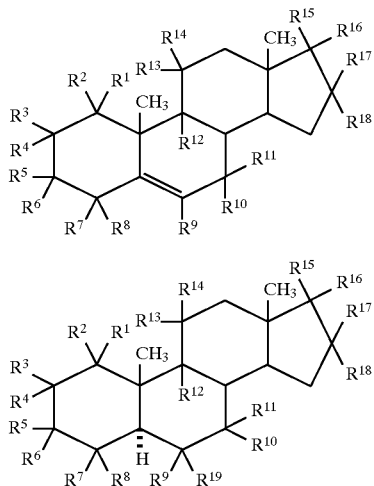

wherein $R^1, R^2, R^3, R^4, R^6, R^7, R^8, R^9, R^{10}, R^{12}, R^{13}, R^{14}$ and $R^{19}$ are independently H, OH, halogen, $C_{1-10}$ alkyl or $C_{1-10}$ alkoxy;

$R^5$ and $R^{11}$ are independently OH, SH, H, halogen, pharmaceutically acceptable ester, pharmaceutically acceptable thioester, pharmaceutically acceptable ether, pharmaceutically accceptable thioether, pharmaceutically acceptable inorganic esters, pharmaceutically acceptable monosaccharide, disaccharide or oligosaccharide, spirooxirane, spirothirane, $-OSO_2R^{20}$, $-OPOR^{20}R^{21}$ or $C_{1-10}$ alkyl; or $R^5$ and $R^6$ taken together are =O; or $R^{10}$ and $R^{11}$ taken together are =O;

$R^{15}$ is (1) H, halogen, $C_{1-10}$ alkyl or $C_{1-10}$ alkoxy when $R^{16}$ is $-C(O)OR^{22}$ or (2) H, halogen, OH or $C_{1-10}$ alkyl when $R^{16}$ is halogen, OH or $C_{1-10}$ alkyl or (3) H, halogen, $C_{1-10}$ alkyl, $C_{1-10}$ alkenyl, $C_{1-10}$ alkynyl, formyl, $C_{1-10}$ alkanoyl or epoxy when $R^{16}$ is OH; or (4) OH, SH, H, halogen, pharmaceutically acceptable ester, pharmaceutically acceptable thioester, pharmaceutically acceptable ether, pharmaceutically accceptable thioether, pharmaceutically acceptable inorganic esters, pharmaceutically acceptable monosaccharide, disaccharide or oligosaccharide, spirooxirane, spirothirane, $-OSO_2R^{20}$ or $-OPOR^{20}R^{21}$ when $R^{16}$ is H; or $R^{15}$ and $R^{16}$ taken together are =O;

$R^{17}$ and $R^{18}$ are independently (1) H, —OH, halogen, $C_{1-10}$ alkyl or $C_{1-10}$ alkoxy when $R^6$ is H, OH, halogen, $C_{1-10}$ alkyl or $-C(O)OR^{22}$ or (2) H, $(C_{1-10}$ alkyl$)_n$amino, $(C_{1-10}$ alkyl$)_n$amino-$C_{1-10}$ alkyl, $C_{1-10}$ alkoxy, hydroxy-$C_{1-10}$ alkyl, $C_{1-10}$ alkoxy-$C_{1-10}$ alkyl, (halogen$)_m$-$C_{1-10}$ alkyl, $C_{1-10}$ alkanoyl, formyl, $C_{1-10}$ carbalkoxy or $C_{1-10}$ alkanoyloxy when $R_{15}$ and $R^{16}$ taken together are =O; or $R^{17}$ and $R^{18}$ taken together are =O or taken together with the carbon to which they are attached form a 3–6 member ring containing 0 or 1 oxygen atom; or $R^{15}$ and $R^{17}$ taken together with the carbons to which they are attached form an epoxide ring;

$R^{20}$ and $R^{21}$ are independently OH, pharmaceutically acceptable ester or pharmaceutically acceptable ether;

$R^{22}$ is H, (halogen$)_m$-$C_{1-10}$ alkyl or $C_{1-10}$ alkyl;

n is 0, 1 or 2; and m is 1, 2 or 3.

2. The method of claim 1, wherein $R^{15}$ and $R^{16}$ together are =O.

3. The method of claim 2, wherein, $R^5$ is OH.

4. The method of claim 2, wherein, $R^5$ is $-OSO_2R^{20}$.

5. The method of claim 4, wherein $R^{20}$ is H.

6. The method of claim 1, wherein the compound is administered intavenously.

7. The method of claim 1, wherein the compound is administered intramuscularly.

8. The method of claim 1, wherein the compound is administered intranasaly.

9. The method of claim 1, wherein the compound is administered intraocularly.

10. The method of claim 1, wherein the compound is administered as an inhalant.

11. The method of claim 1, wherein the compound is administered in the amount of 1–1000 mg/kg.

12. The method of claim 1, wherein the compound is administered in the amount of 2–200 mg/kg.

13. The method of claim 1, wherein the compound is administered in an amount to deliver an effective DHEA dose of 0.1–100 mg/kg.

14. The method of claim 1, wherein the compound is administered in an amount to deliver an effective DHEA dose fo 1–50 mg/kg.

15. The method of claim 1, wherein the compound is administered in an amount to deliver an effective DHEA dose fo 2–20 mg/kg.

* * * * *